(12) United States Patent
Russell et al.

(10) Patent No.: US 9,695,432 B2
(45) Date of Patent: Jul. 4, 2017

(54) EXCISION OF TRANSGENES IN GENETICALLY MODIFIED ORGANISMS

(75) Inventors: Sean M. Russell, Indianapolis, IN (US); Joseph F. Petolino, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 1132 days.

(21) Appl. No.: 13/011,666

(22) Filed: Jan. 21, 2011

(65) Prior Publication Data

US 2011/0191877 A1 Aug. 4, 2011

Related U.S. Application Data

(60) Provisional application No. 61/297,628, filed on Jan. 22, 2010.

(51) Int. Cl.
*C12N 15/82* (2006.01)
*C12N 9/22* (2006.01)
*A01H 1/02* (2006.01)

(52) U.S. Cl.
CPC ........... *C12N 15/8213* (2013.01); *A01H 1/02* (2013.01); *C12N 9/22* (2013.01); *C12N 15/8241* (2013.01); *C12N 15/8265* (2013.01)

(58) Field of Classification Search
None
See application file for complete search history.

(56) References Cited

U.S. PATENT DOCUMENTS

| | | |
|---|---|---|
| 5,723,765 A | 3/1998 | Oliver et al. |
| 5,925,808 A | 7/1999 | Oliver et al. |
| 5,977,441 A | 11/1999 | Oliver et al. |
| 7,348,179 B2 | 3/2008 | Gleba et al. |
| 7,525,015 B2 | 4/2009 | Luo et al. |
| 2007/0134796 A1 | 6/2007 | Holmes et al. |

FOREIGN PATENT DOCUMENTS

| | | |
|---|---|---|
| WO | 2005049842 A2 | 6/2005 |
| WO | 2006105946 A2 | 10/2006 |
| WO | 2008145757 A1 | 12/2008 |
| WO | 2009006297 A2 | 1/2009 |
| WO | 2009042164 A1 | 4/2009 |
| WO | 2009111263 A1 | 9/2009 |

OTHER PUBLICATIONS

Carroll 2011 Genetics 188: p. 773-782.*
Cai et al 2009 Plant Molecular Biology 69: p. 699-709.*
Zhang et al 2003 Theoretical and Applied Genetics 107:7 p. 1157-1168.*
Moon et al Oct. 2009 Trends in Biotechnology 28:1 p. 3-8.*
Puchta 2005 Journal of Experimental Botany 56:409 p. 1-14.*
Ramirez et al 2008 Nature Methods 5:5 p. 374-375.*
Isalan, M 2012 (Nature Methods 9: p. 32-34).*
Bibikova et al., "Stimulation of homologous recombination through targeted cleavage by chimeric nucleases," Molecular and Cellular Biology, Jan. 2001, pp. 289-297, vol. 21, No. 1.
Durai et al., "Zinc finger nucleases: custom-designed molecular scissors for genome engineering of plant and mammalian cells," Nucleic Acids research, 2005, pp. 5978-5990, vol. 33, No. 18.
Gilbertson, "Cre-lox recombination: cre-ative tools for plant biotechnology," Trends in Biotechnology, Dec. 2003, pp. 550-555, vol. 21, No. 12.
Hare et al., "Excision of selectable marker genes from transgenic plants," Nature Biotechnology, Jun. 2002, pp. 575-580, vol. 20.
Hills et al., "Genetic use restriction technologies (GURTs): strategies to impede transgene movement," Trends in Plant Science, Mar. 13, 2007, pp. 177-183, vol. 12, No. 4.
Hoff et al., "A recombinase-mediated transcriptional induction system in transgenic plants," Plant Molecular Biology, 201, pp. 41-49, vol. 45.
Katada et al., "Artificial restriction DNA cutters as new tools for gene manipulation," ChemBioChem, 2009, pp. 1279-1288, vol. 10.
Keenan et al., "Nontransgenic crops form transgenic plants," Nature Biotechnology, Mar. 2002, pp. 215-216, vol. 20.
Lee et al., "Evaluating genetic containment strategies for transgenic plants," Trends in Biotechnology, Mar. 2006, pp. 109-114, vol. 24, No. 3.
Lu, "Transgene containment by molecular means—is it possible and cost effective?," Environ. Biosafety Res., 2003, pp. 3-8, vol. 2.
Luo et al., "GM-gene-deletor: fused loxP-FRT recognition sequences dramatically imporve the efficiency of FLP or CRE recombinase on transgene excision from pollen and seed of tobacco plants," Plant Biotechnology Journal, 2007, pp. 263-275, vol. 5.
Mlynarova et al., "Directed microspore-specific recombination of transgenic alleles to prevent pollen-mediated transmission of transgenes," Plant biotechnology Journal, 2006, pp. 445-452, vol. 4.
Perez et al., "Establishment of HIV-1 resistance in CD4+ T cells by genome editing using zinc-finger nucleases," Nature Biotechnology, Jul. 2008, pp. 808-816, vol. 26, No. 7.
Stewart, Jr. et al., "Transgene introgression form genetically modified crops to their wild relatives," Nature Reviews, Oct. 2003, pp. 806-817, vol. 4.
Wu et al, "Custom-designed zinc finger nucleases: what is next," Cell. Mol. Life Sci. 2007, pp. 2933-2944, vol. 64.
Kandavelou, Karthikeyan et al., "Targeted manipulation of mammalian genomes using designed zinc finger nucleases", Biochemical and Biophysical Research Communications, 2009, pp. 56-61, vol. 388.

(Continued)

*Primary Examiner* — Matthew Keogh
(74) *Attorney, Agent, or Firm* — Sean M. Russell; Eric J. Kraus; Magleby Cataxinos & Greenwood

(57) ABSTRACT

A method for deleting a region of DNA in a plant. In some embodiments, the method comprises transforming a plant with a nucleic acid molecule, wherein the nucleic acid molecule encodes one or more zinc finger nuclease(s) (ZFNs) operably linked to one or more tissue-specific promoter(s), e.g., a pollen-specific promoter. Methods include excising native genes in a plant. Accordingly, in some embodiments, ZFNs are engineered that recognize sequences that flank native plant genes. In further embodiments, ZFNs are expressed under the control of developmental stage-specific promoters, such that, for example, nucleic acid sequences are specifically excised in plants during relatively late stages of development. Nucleic acid molecules useful for carrying out disclosed methods and plants produced by the methods are included.

13 Claims, 17 Drawing Sheets

(56) References Cited

OTHER PUBLICATIONS

Kim, Hye Joo et al., "Targeted genome editing in human cells with zinc finger nucleases constructed via modular assembly", Genome Research, 2009, pp. 1279-1288, vol. 19.

Pruett-Miller, Shondra M et al., "Comparison of Zinc Finger Nucleases for Use in Gene Targeting in Mammalian Cells", Molecular Therapy, Mar. 4, 2008, pp. 707-717, vol. 16 No. 4.

Tovkach, Andriy et al., "A toolbox and procedural notes for characterizing novel zinc finger nucleases for genome editing in plant cells",The Plant Journal, 2009, pp. 747-757, vol. 57.

Townsend, Jeffrey A. et al., "High-frequency modification of plant genes using engineered zinc-finger nucleases", Nature, May 21, 2009, pp. 442-446, vol. 459.

International Search Report for International Application No. PCT/US2011/022135, mailed Sep. 28, 2011.

Written Opinion for International Application No. PCT/US2011/022135, mailed Sep. 28, 2011.

Lloyd, Alan et al., "Targeted mutagenesis using zinc-finger nucleases in Arabidopsis," PNAS, Feb. 8, 2005, vol. 102, No. 6.

Supplementary European Search Report for European Patent Application No. 11735267.4, dated Jun. 24, 2013, 10 pages.

Philip, Gregory D. et al., "Editing the genome of crop plants with engineered zinc finger proteins," In Vitro Cellular & Developmental Biology, Jun. 1, 2009, pp. S27, vol. 45, No. Suppl. 1.

Kandavelou, Karthikeyan, et al., "Custom-designed molecular scissors for site-specific manipulation of the plant and mammalian genomes," Methods in Molecular Biology, Jan. 1, 2009, pp. 617-636, vol. 544.

Shukla, Vipula K, et al., "Precise genome modification in the crop species *Zea mays* using zinc-finger nucleases," International Weekly Journal of Science, Nature Publishing Group, May 21, 2009, p. 437, vol. 459, No. 7245.

Wright, D. A. et al., "High-frequency homologous recombination in plants mediated by zinc-finger nucleases," The Plant Journal, Blackwell Scientific Publications, Nov. 1, 2005, pp. 693-705, vol. 44, No. 4.

\* cited by examiner

GFP Scores   GUS Scores

EXCISION OF TRANSGENES IN GENETICALLY MODIFIED ORGANISMS

CROSS-REFERENCE TO RELATED APPLICATION

This application claims the benefit of U.S. Provisional Patent Application Ser. No. 61/297,628, filed Jan. 22, 2010, the disclosure of which is hereby incorporated herein in its entirety by this reference.

FIELD OF THE INVENTION

The invention generally relates to compositions and methods for generating transgenic plants. In certain embodiments, the transgenic plants comprise one or more transgenes of interest. In certain embodiments, excision of transgene(s) is directed in pollen and/or seed, such that the pollen and/or seed produced by a transgenic plant of the invention is substantially free of transgene(s). In some embodiments, transgenic plants of the invention are useful, for example, in achieving bioconfinement of transgene(s) of interest in the transgenic plant. In other embodiments, the excision of the transgene is directed to a specific expression cassette, such as a selectable marker, such that only this expression cassette is removed from the transgenic plant and/or progeny of the transgenic plant.

BACKGROUND

Many plants are genetically transformed with genes from other species to introduce desirable traits, such as to improve agricultural value through, e.g., improving nutritional value quality, increasing yield, conferring pest or disease resistance, increasing drought and stress tolerance, improving horticultural qualities such as pigmentation and growth, and/or imparting herbicide resistance; enabling the production of industrially useful compounds and/or materials from the plant; and/or enabling the production of pharmaceuticals. The introduction of cloned genes into plant cells and recovery of stable fertile transgenic plants can be used to make such modifications of a plant, and has allowed desirable traits or qualities of interest to be incorporated into plants via genetic engineering (e.g., crop improvement). In these methods, foreign DNA is typically introduced into the nuclear or plastid DNA of the eukaryotic plant cell, followed by isolation of cells containing the foreign DNA integrated into the cell's DNA, to produce stably transformed plant cells.

One drawback that arises regarding the use of transgenic plants is the possibility of transgene escape to wild species and non-transformed species. These traits can increase the risk of outcrossing, persistence, and introgression of transgenes into an adjacent population. The escape of transgenes from genetically modified (GM) crops usually occurs through gene flow, mainly by cross-pollination (Lu (2003) *Eviron. Biosafety Res.* 2:3-8), but may also occur through introgression. Stewart Jr. et al. (2003) *Nat. Reviews Gen.* 4:806-17. Crop-to-crop gene flow will result in contamination of non-GM varieties, affecting the strategic deployment of transgenic and non-transgenic crop varieties in a given agricultural system. Significant contamination of non-GM crops with transgenic material poses difficulties in international trade because of legal restrictions on imports of transgenic products by many countries. Crop-to-crop gene flow can cause stacking of transgenes in hybrids that may potentially become volunteer weeds if the transgenes impart multiple resistance (e.g., to herbicides, pests, and/or diseases). Additionally, crop-to-crop gene flow will lead to transgene escape into weedy populations or related wild species, which may pose serious weed problems and other ecological risks if the transgenes persist and establish in the weedy/wild populations through sexual reproduction and/or vegetative propagation. This is a particular concern when escaped genes enhance the ecological fitness of the weedy/wild species. Introgression of a crop transgene occurs in steps involving several successive hybrid generations. Introgression is a dynamic process that may take many years and generations before the transgene is fixed in the genetic background of a receiving species and, thus, presents difficulties of detection and monitoring. However, if selection is strong and/or population size is small, fixation of an introgressed gene may occur rapidly.

Containment of a specific expression cassette within genetically modified plants, especially a selectable marker expression cassette, is an elusive goal. Selectable marker genes are usually antibiotic resistant or herbicide tolerant genes, but may include reporter genes (i.e., β-glucuronidase (Graham et al. (1989) *Plant Cell Tiss. Org.* 20(1):35-39). Selectable makers which are co-transferred into the genome of a plant provide a selective advantage and allow for the identification of stably transformed transgenic plants. The availability of functional selectable maker genes which can be used for the transformation of plants is somewhat limited. A review of the published scientific literature on transgenic crop plants reveals that the most widely used selective agents for antibiotic resistance are for kanamycin (encoded by the neomycin phosphotransferase type II gene (Bevan et al. (1983) *Nature* 304:184-187)) or hygromycin (encoded by the hygromycin phosphotransferase gene (Waldron et al., *Plant Mol. Biol.* 5:103-108)), and herbicide tolerance is phosphinothricin resistance (encoded by the pat (Wohlleben et al. (1988) *Gene* 70:25-37) or bar genes (DeBlock et al. (1987), *EMBO J.* 6 (9):2513-2518)). See, Sundar et al. (2008) *J. Plant Physiol.* 165:1698-1716. Given the limited number of selectable marker genes and the common use of a sub-set of these traits, a solution that allows for the excision and re-use of selectable markers within a transgenic plant would obviate the need for additional selectable makers in subsequent rounds of gene transfer or gene stacking into the same plant. Moreover, the ability to excise a selectable marker could overcome unintended changes to the plant transcriptome that are caused by the expression of the marker (Abdeen et al. (2009) *Plant Biotechnol. J.* 7(3):211-218).

Current strategies to prevent or minimize gene flow between GM crops and other species and varieties include: (1) physical isolation of the transgenic crop; (2) chloroplast engineering of transgenes; (3) co-engineering of a mitigation gene along with the transgene; (4) genetic use restriction technologies (GURTs); (5) CRE/loxP and FLP/FRT recombinase-mediated gene deletion. See, e.g., Lee and Natesan (2006) *TRENDS Biotech.* 24(3):109-14; Lu (2003), supra; and Luo et al. (2007), *Plant Biotech. J.* 5:263-74; and (6) meganuclease-mediated gene deletion. See, e.g., U.S. patent application Ser. No. 11/910,515; and U.S. patent application Ser. No. 12/600,902.

CRE, FLP, and R recombinases have been exploited for the excision of unwanted genetic material from plants. Hare and Chua (2002) *Nat. Biotech.* 20:575-80. Luo et al. (2007), supra, reported a pollen- and seed-specific "GM-gene-deletor" system, wherein use of loxP-FRT fusion sequences as recognition sites for excision of transgenes by CRE or FLP recombinase led to deletion of transgenes from pollen, or from both pollen and seed, of transgenic tobacco plants. All these site-specific recombinase systems shown to function in plants are members of the integrase family. These systems have been chosen for use, at least in part, due to the fact that other recombinases may require ancillary proteins and more complex recognition sites that may confer topological restraints on recombination efficiencies. Id. These systems have several significant drawbacks: integrase-type recombinases may also recognize "pseudo-sequences," which may be highly divergent from a specific target sequence and, therefore, lead to unwanted non-specific DNA deletions; and excision of a target sequence leaves a residual recognition sequence that may be sites of chromosomal rearrangements upon subsequent exposure to the recombinase, or activate gene silencing mechanisms. Id. Moreover, these systems are further constrained as a functional recombinase must be present and expressed in one of the parent plants, the presence of which requires additional strategies for deletion within pollen and/or seed. Despite these limitations, the CRE/loxP system is recognized as the most suitable strategy for optimization of gene deletion in plants. Id.

Custom-designed zinc finger nucleases (ZFNs) are proteins designed to deliver a targeted site-specific double-strand break in DNA, with subsequent recombination of the cleaved ends. ZFNs combine the non-specific cleavage domain of FokI restriction endonuclease with zinc finger DNA-binding proteins. See, e.g., Huang et al. (1996) *J. Protein Chem.* 15:481-9; Kim et al. (1997) *Proc. Natl. Acad. Sci. USA* 94:3616-20; Kim et al. (1996) *Proc. Natl. Acad. Sci. USA* 93:1156-60; Kim et al. (1994) *Proc. Natl. Acad. Sci. USA* 91:883-7; Kim et al. (1997b) *Proc. Natl. Acad. Sci. USA* 94:12875-9; Kim et al. (1997c) *Gene* 203:43-9; Kim et al. (1998) *Biol. Chem.* 379:489-95; Nahon and Raveh (1998) *Nucleic Acids Res.* 26:1233-9; Smith et al. (1999) *Nucleic Acids Res.* 27:674-81. Individual zinc finger motifs can be designed to target and bind to a large range of DNA sites. $Cys_2His_2$ zinc finger proteins bind DNA by inserting an α-helix into the major groove of the double helix. Recognition of DNA by zinc fingers is modular: each finger contacts primarily three consecutive base pairs in the target, and a few key residues in the protein mediate recognition. It has been shown that FokI restriction endonuclease must dimerize via the nuclease domain in order to cleave DNA, inducing a double-strand break. Similarly, ZFNs also require dimerization of the nuclease domain in order to cut DNA. Mani et al. (2005) *Biochem. Biophys. Res. Commun.* 334: 1191-7; Smith et al. (2000) *Nucleic Acids Res.* 28:3361-9. Dimerization of the ZFN is facilitated by two adjacent, oppositely oriented binding sites. Id. In addition, double strand breaks caused by zinc finger nucleases are resolved by the plants DNA repair machinery via either nonhomologous end joining (NHEJ) or homology directed repair (HDR), thereby resulting in plants which are free of residual recognition sequences.

SUMMARY OF THE DISCLOSURE

According to an embodiment of the invention, a method for deleting a region of DNA in a plant wherein a viable plant containing a genomic DNA, the genomic DNA comprising the region of DNA, is provided; and a zinc finger nuclease, engineered to cleave the genomic DNA at a recognition sequence, is expressed or introduced in the viable plant containing the genomic DNA; thereby resulting in cleavage of the genomic DNA at recognition sequences resulting in the excision of the genomic DNA, wherein the region of DNA is absent from the genomic DNA.

In another embodiment, a method for deleting a region of DNA in a plant includes providing a first viable plant containing a genomic DNA, the genomic DNA comprising the region of DNA and a first recognition sequence flanking the 3' end and a second recognition sequence flanking the 5' end of the region of DNA. A second viable plant containing a genomic DNA is provided, the genomic DNA comprising a DNA encoding a zinc finger nuclease engineered to cleave the genomic DNA at the recognition sequences. The first and second viable plants are crossed such that F1 seed is produced on either the first or the second viable plant. A resultant F1 plant containing a genomic DNA is grown, wherein the region of DNA is absent from the genomic DNA. In certain embodiments, the first recognition sequence and the second recognition sequence can be identical.

In a particular embodiment, an isolated nucleic acid molecule includes: a first nucleic acid sequence recognized by a zinc finger nuclease; a gene of interest; and a second nucleic acid sequence recognized by a zinc finger nuclease, wherein the gene of interest is flanked by the first and second nucleic acid sequences recognized by a zinc finger nuclease. In another embodiment, the first recognition sequence and the second recognition sequence can be flanked by homologous sequences. In yet another embodiment, a method of producing a transgenic plant includes transforming a plant cell or plant tissue with the isolated nucleic acid molecule and regenerating a whole plant.

In an additional embodiment, a method for reducing the transmission of a gene of interest to other plants includes crossing the whole plant with a plant regenerated from a plant cell or tissue transformed with an isolated nucleic acid molecule comprising a pollen-specific promoter operably linked to a zinc finger nuclease, wherein the gene of interest is specifically excised in pollen of the progeny resulting from the cross. The progeny resulting from the cross are cultivated. In such embodiment, an isolated nucleic acid molecule includes a promoter and a nucleic acid sequence encoding a zinc finger nuclease, wherein the promoter is operably linked to the nucleic acid sequence encoding the zinc finger nuclease and the method of producing a transgenic plant that includes transforming a plant cell or plant tissue with the isolated nucleic acid molecule and regenerating a whole plant.

In an embodiment, a method for deleting a region of DNA in a plant containing a nucleic acid molecule including: a first nucleic acid sequence recognized by a zinc finger nuclease; a selectable marker gene expression cassette; and a second nucleic acid sequence recognized by a zinc finger nuclease, wherein the selectable marker is flanked by the first and second nucleic acid sequences recognized by a zinc finger nuclease. In another embodiment, the first recognition sequence and the second recognition sequence are flanked by homologous sequences. Additionally, a zinc finger nuclease, engineered to cleave the genomic DNA at a recognition sequence, is expressed or introduced in the viable plant cell; thereby resulting in cleavage of the genomic DNA at recognition sequences resulting in the excision of the genomic DNA, wherein the selectable marker is absent from the genomic DNA.

In another embodiment, each half of the zinc finger nuclease monomer is expressed separately and when paired in conjunction with one another form a functional complex. For example, a plant transcription unit which expresses one zinc finger nuclease monomer (consisting of a zinc finger binding motif operably linked to the FokI endonuclease) is stably integrated into one parent, P1, and a plant transcription unit which expresses a second monomer is stably integrated into a second parent, P2. The sexual cross of P1×P2 results in progeny plants which contain both zinc finger monomers. The resulting zinc finger nuclease dimer is capable of binding to a zinc finger binding site and forming a complex which has cleavage activity. Given that the FokI endonuclease is active as a dimer (Bitinaite et al. (1998) *Proc. Natl. Acad. Sci. USA* 95:10,570-10,575), the cleavage activity is only capable of occurring within progeny which contain both functionally expressing monomers.

In another embodiment, the excision by a zinc finger nuclease at a recognition sequence results in the formation of a cleavage junction, which is free of a residual recognition sequence. The cleavage junction may not be bound and cleaved by the original zinc finger nuclease(s). Additionally, the cleavage junction can be the result of non-homologous end joining (NHEJ) or the result of homology directed repair between two homologous regions of DNA which are located upstream of the 5' recognition sequence and downstream of the 3' recognition sequence or the result of another undescribed DNA repair mechanism. A homologous sequence can be placed outside binding sites so that after cleavage, homology directed repair can occur. This is an improvement over recombinase systems, which always leave behind a remnant of the site used to get the excision.

In yet another embodiment, a method of excising a native gene of interest in a plant includes transforming a plant cell or tissue comprising a gene of interest with an isolated nucleic acid molecule comprising a nucleic acid sequence encoding a zinc finger nuclease or an isolated protein sequence which encodes a zinc finger nuclease, wherein the zinc finger nuclease recognizes a nucleic acid sequence flanking the native gene of interest and the native gene of interest is specifically excised. A whole plant is then regenerated. In an alternative embodiment, endogenous gene excision can be accomplished by crossing a plant expressing a zinc finger nuclease with a target plant.

BRIEF DESCRIPTION OF THE FIGURES

FIGS. 7a and 7b include an alignment of sequence analysis of the 2.4 kb band showing deletion of the GUS expression cassette according to an embodiment of the invention. The bold sequence indicates the At Actin Promoter and MAR gene elements. CCR5 binding sites are identified with underlining and italics. Although multiple amplicons were generated and sequenced per event, only one amplicon was aligned in the Figures.

SEQUENCE LISTING

Figure 1:
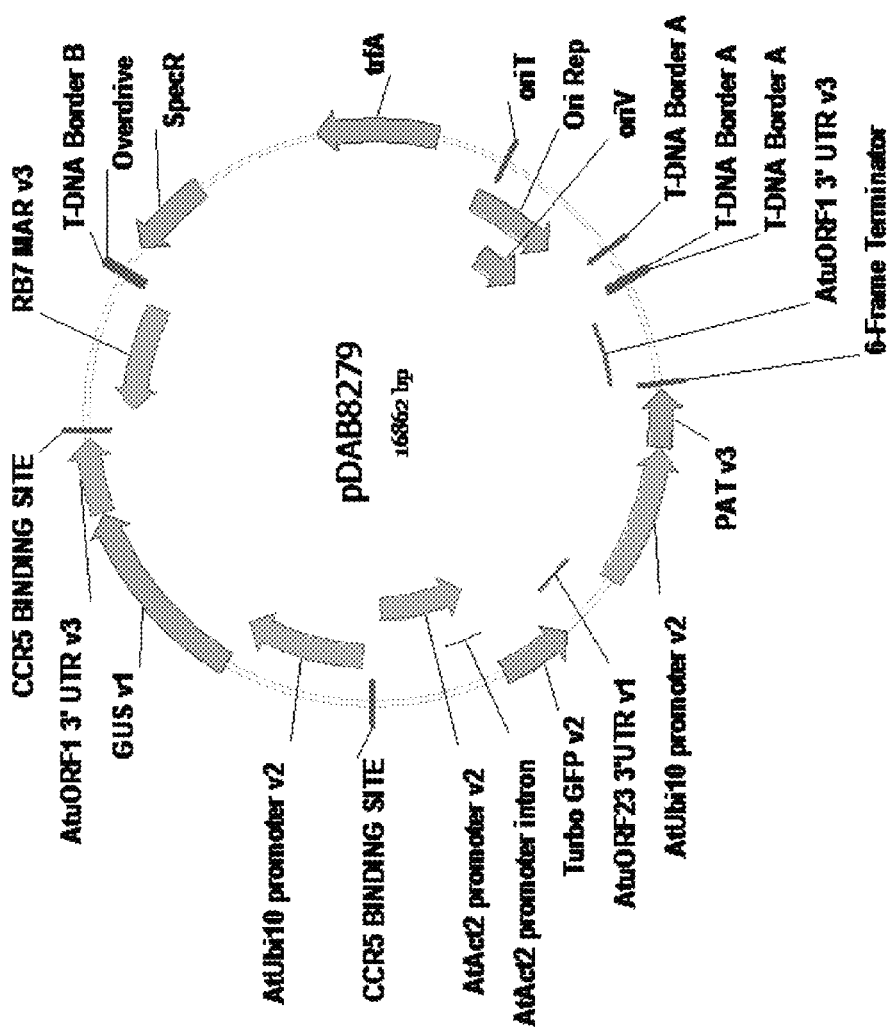
FIG. 1 includes the plasmid map for plasmid pDAS5380.

The nucleic acid sequences listed in the accompanying sequence listing are shown using standard letter abbreviations for nucleotide bases. Only one strand of each nucleic acid sequence is shown, but the complementary strand is understood as being included by any reference to the displayed strand. In the accompanying sequence listing:

SEQ ID NO:1 shows a CCR5ZFN binding site.
SEQ ID NO:2 shows a CCR5Zinc Finger Nuclease gene sequence.
SEQ ID NO:3 shows a TQPATS primer.
SEQ ID NO:4 shows a TQPATA primer.
SEQ ID NO:5 shows a TQPATFQ primer.
SEQ ID NO:6 shows a TQPALS primer.
SEQ ID NO:7 shows a TQPALA primer.
SEQ ID NO:8 shows a TQPALFQ primer.
SEQ ID NO:9 shows a HPT2S primer.
SEQ ID NO:10 shows a HPT2A primer.
SEQ ID NO:11 shows a HPTFQ primer.
SEQ ID NO:12 shows a Fok1_UPL_F primer.
SEQ ID NO:13 shows a Fok1_UPL_R primer.
SEQ ID NO:14 shows a BY2ACT89S primer.
SEQ ID NO:15 shows a BY2ACT89A primer.

SEQ ID NO:16 shows a forward PCR primer for PTU PCR analysis.

SEQ ID NO:17 shows a reverse PCR primer for PTU PCR analysis.

SEQ ID NO:18 shows a BYACTFQ primer.

DETAILED DESCRIPTION

Disclosed herein is a method to excise genes from specific plant tissue in genetically modified organisms. In some embodiments, one or more ZFNs (zinc finger nuclease) are used to remove transgenes from specific plant tissue as a means of reducing gene flow into non-GM crops. In some embodiments, the transgene that is removed is a selectable marker gene cassette. In certain embodiments, the specific plant tissue is pollen.

In some embodiments, one or more ZFNs may be operably linked to different tissue-specific promoters. In these and further embodiments, one of the one or more ZFNs operably linked to a tissue-specific promoter may be transformed into one parent plant line, and another of the one or more ZFNs operably linked to a different tissue-specific promoter may be transformed into a second parent plant line. A cross between the parental lines containing each of the one or more ZFNs can produce an $F_1$ line that contains a functional ZFN that cleaves DNA at a recognition sequence. The recognition sequences may flank transgenes in the DNA of the plant.

Tissue-specific gene excision may be achieved by operable linkage of tissue-specific plant promoters to ZFNs. In some embodiments, operable linkage of a tissue-specific promoter to one or more ZFNs leads to tissue-specific expression of the one or more ZFNs, thereby excising the ZFNs, selectable markers, and/or any genes or nucleic acid sequences located between the recognition sequences in the specific tissue.

In particular embodiments, one or more ZFNs are expressed within the same plant. ZFNs may be operably linked to promoters that drive expression of the ZFNs during later developmental stages of a plant. In these and other embodiments, one or more functional ZFNs may cleave specific recognition sequences that flank one or more transgene(s), thereby removing the one or more transgenes from plant tissue during later stages of plant development.

Abbreviations

| | |
|---|---|
| GM | Genetically modified |
| PTU | Plant transcription unit |
| ZF | Zinc finger |
| ZFN | Zinc finger nuclease |
| ZFP | Zinc finger protein |

Terms

Gene expression: The process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

Hybridization: Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{2+}$ concentration) of the hybridization buffer will contribute to the stringency of hybridization, though wash times also influence stringency. Calculations regarding hybridization conditions required for attaining particular degrees of stringency are discussed in Sambrook et al. (ed.), *Molecular Cloning: A Laboratory Manual*, 2nd ed., vol. 1-3, Cold Spring Harbor Laboratory Press, Cold Spring Harbor, N.Y., 1989, chs. 9 and 11.

For purposes of the present disclosure, "stringent conditions" encompass conditions under which hybridization will occur if there is less than 25% mismatch between the hybridization molecule and the target sequence. "Stringent conditions" can be further defined into particular levels of stringency. Thus, as used herein, "moderate stringency" conditions are those under which molecules with more than 25% mismatch will not hybridize; conditions of "medium stringency" are those under which molecules with more than 15% mismatch will not hybridize, and conditions of "high stringency" are those under which sequence with more than 10% mismatch will not hybridize. Conditions of "very high stringency" are those under which sequences with more than 6% mismatch will not hybridize.

In particular embodiments, stringent conditions are hybridization at 65° C., followed by sequential washes at 65° C. with 0.1×SSC/0.1% SDS for 40 minutes.

Isolated: An "isolated" biological component (such as a nucleic acid or protein) has been substantially separated, produced apart from, or purified away from other biological components in the cell of the organism in which the component naturally occurs, i.e., other chromosomal and extra-chromosomal DNA and RNA, and proteins. Nucleic acid molecules and proteins that have been "isolated" include nucleic acid molecules and proteins purified by standard purification methods. The term also embraces nucleic acids and proteins prepared by recombinant expression in a host cell, as well as chemically synthesized nucleic acid molecules, proteins, and peptides.

Nucleic acid molecule: A polymeric form of nucleotides, which can include both sense and anti-sense strands of RNA, cDNA, genomic DNA, and synthetic forms and mixed polymers of the above. A nucleotide refers to a ribonucleotide, deoxynucleotide, or a modified form of either type of nucleotide. A "nucleic acid molecule" as used herein is synonymous with "nucleic acid" and "polynucleotide." The term includes single- and double-stranded forms of DNA. A nucleic acid molecule can include either or both naturally occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications, such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., peptides), intercalators (e.g., acridine, psoralen, etc.), chelators, alkylators, and modified linkages (e.g., alpha anomeric nucleic acids, etc.). The term "nucleic acid molecule" also includes any topological conformation, including single-stranded, double-stranded, partially duplexed, triplexed, hairpinned, circular, and padlocked conformations.

Operably linked: A first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

Promoter: A region of DNA that generally is located upstream (towards the 5' region of a gene) that is needed for transcription. Promoters permit the proper activation or repression of the gene which they control. A promoter contains specific sequences that are recognized by transcription factors. These factors bind to the promoter DNA sequences and result in the recruitment of RNA polymerase, the enzyme that synthesizes the RNA from the coding region of the gene. In some embodiments, tissue-specific promoters are used in methods of the invention, e.g., a pollen-specific promoter. A tissue-specific promoter is a DNA sequence that directs a higher level of transcription of an associated gene in the tissue for which the promoter is specific relative to the other tissues of the organism. Examples of tissue-specific promoters include tapetum-specific promoters; anther-specific promoters; pollen-specific promoters (see, e.g., U.S. Pat. No. 7,141,424, and International PCT Publication No. WO 99/042587); ovule-specific promoters; (see, e.g., U.S. Patent Application No. 2001/047525 A1); fruit-specific promoters (See, e.g., U.S. Pat. Nos. 4,943,674, and 5,753,475); and seed-specific promoters (see, e.g., U.S. Pat. Nos. 5,420, 034, and 5,608,152). In some embodiments, developmental stage-specific promoters are used in methods of the invention, e.g., a promoter active at a later stage in development.

Transformed: A virus or vector "transforms" or "transduces" a cell when it transfers nucleic acid molecules into the cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to, transfection with viral vectors, transformation with plasmid vectors, electroporation (Fromm et al. (1986) *Nature* 319:791-3), lipofection (Felgner et al. (1987) *Proc. Natl. Acad. Sci. USA* 84:7413-7), microinjection (Mueller et al. (1978) *Cell* 15:579-85), *Agrobacterium*-mediated transfer (Fraley et al. (1983) *Proc. Natl. Acad. Sci. USA* 80:4803-7), direct DNA uptake, and microprojectile bombardment (Klein et al. (1987) *Nature* 327:70).

Transgene: An exogenous nucleic acid sequence. In one example, a transgene is a gene sequence (e.g., a herbicide-resistance gene), a gene encoding an industrially or pharmaceutically useful compound, or a gene encoding a desirable agricultural trait. In yet another example, the transgene is an antisense nucleic acid sequence, wherein expression of the antisense nucleic acid sequence inhibits expression of a target nucleic acid sequence. A transgene may contain regulatory sequences operably linked to the transgene (e.g., a promoter).

Vector: A nucleic acid molecule as introduced into a cell, thereby producing a transformed cell. A vector can include nucleic acid sequences that permit it to replicate in the host cell, such as an origin of replication. Examples include, but are not limited to, a plasmid, cosmid, bacteriophage, or virus that carries exogenous DNA into a cell. A vector can also include one or more genes, antisense molecules, and/or selectable marker genes and other genetic elements known in the art. A vector can transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coding, etc.).

Zn-Finger Nuclease-Mediated Excision of Transgenes from Plants

Disclosed herein are methods for producing a plant having decreased transgene escape, as well as plants produced by such methods, and plant materials derived therefrom, e.g., seeds. In one embodiment, the method comprises contacting a plant with a vector, wherein the vector includes one or more zinc finger nuclease(s) (ZFNs) operably linked to one or more tissue-specific promoter(s) (e.g., a pollen-specific promoter). Expression of this vector results in the production of the ZFN(s) in the specific tissue wherein its operably linked promoter is active. The ZFN(s) may be designed or engineered to recognize a cleavage sequence that flanks a nucleic acid sequence, the excision of which is desired. Production of the ZFN(s), then, in the specific tissue wherein the promoter is active, results in excision of the nucleic acid sequence between the cleavage sequences recognized by the ZFN(s), thereby producing a nucleic acid sequence that contains a cleavage junction that is free of a residual recognition sequence.

In another embodiment, the method comprises: contacting a plant with a vector, wherein the vector includes one or more ZFN(s) operably linked to a tissue-specific promoter; a gene of interest; optionally one or more regulatory element(s) that may be operably linked to the gene of interest; and one or more cleavage sequences recognized by the ZFN(s) flanking the gene of interest and the one or more regulatory element(s). Expression of this vector results in the production of the ZFN(s) in the specific tissue wherein its operably linked promoter is active. Production of the ZFN(s), then, in the specific tissue wherein the promoter is active results in excision of the nucleic acid sequence between the cleavage sequences recognized by the ZFN(s), which includes the gene of interest and, optionally, the one or more regulatory element(s).

In further embodiments, the method comprises contacting a plant with a vector, wherein the vector includes one or more zinc finger nuclease(s) (ZFNs) operably linked to one or more promoter(s) active at a particular period of plant development (e.g., a promoter that drives expression at a relatively late stage of development). Expression of this vector results in the production of the ZFN(s) during the specific period of development wherein its operably linked promoter is active. The ZFN(s) may be designed or engineered to recognize a cleavage sequence that flanks a nucleic acid sequence, the excision of which is desired. Production of the ZFN(s) at the developmental stage wherein the promoter is active, results in excision of the nucleic acid sequence between the cleavage sequences recognized by the ZFN(s).

In still further embodiments, the method comprises: contacting a plant with a vector, wherein the vector includes one or more ZFN(s) operably linked to a promoter active at a particular period of plant development; a gene of interest; optionally one or more regulatory element(s) that may be operably linked to the gene of interest; and one or more cleavage sequences recognized by the ZFN(s) flanking the gene of interest and the one or more regulatory element(s). Expression of this vector results in the production of the ZFN(s) during the specific period of development wherein its operably linked promoter is active. Production of the ZFN(s) during the specific period of development wherein its operably linked promoter is active, results in excision of the nucleic acid sequence between the cleavage sequences recognized by the ZFN(s), which includes the gene of interest and the one or more regulatory element(s).

ZFN Nucleases

In particular embodiments, ZFNs are expressed from nucleic acid molecules in transformed plants to direct the excision of nucleic acid sequences in the transformed plants. ZFNs may be used that target a recognition sequence engineered to flank a particular nucleic acid sequence (e.g., a transgene, gene of interest, or selectable marker gene) or ZFNs may be designed to target a naturally occurring nucleic acid sequence flanking a particular nucleic acid sequence to be excised. The exquisite flexibility and specificity of the ZFN system provides a level of control previously unachievable by known recombinase-mediated gene excision strategies.

Recognition specificities of ZFNs can be easily manipulated experimentally. Wu et al. (2007) Cell. Mol. Life. Sci. 64:2933-44. Randomization of the codons for zinc finger recognition residues allows the selection of new fingers that have high affinity for arbitrarily chosen DNA sequences. Furthermore, zinc fingers are natural DNA-binding molecules, and engineered zinc fingers have been shown to act on their designed targets in living cells. Thus, nucleases based on zinc fingers are targetable to specific but arbitrary recognition sites.

The requirement for dimerization of cleavage domains of chimeric zinc finger nucleases imparts a high level of sequence specificity. Since each set of three fingers binds nine consecutive base pairs, two chimeric nucleases effectively demand an 18 bp target if each zinc finger domain has perfect specificity. Any given sequence of this length is predicted to be unique within a single genome (assuming approximately $10^9$ bp). Bibikova et al. (2001) Mol. Cell. Biol. 21(1):289-97; Wu et al. (2007), supra. Furthermore, additional fingers provide enhanced specificity, Beerli et al. (1998) Proc. Natl. Acad. Sci. USA 95:14628-33; Kim and Pabo (1998) Proc. Natl. Acad. Sci. USA 95:2812-7; Liu et al. (1997) Proc. Natl. Acad. Sci. USA 94:5525-30, so the number of zinc fingers in each DNA-binding domain may be increased to provide even further specificity. For example, specificity may be further increased by using a pair of 4-finger ZFNs that recognize a 24 bp sequence. Urnov et al. (2005) Nature 435:646-51.

Key amino acids in ZFNs, at positions −1, 2, 3, and 6 relative to the start of the α-helix, contribute most of the specific interactions by the zinc finger motifs. Pavletich and Pabo (1991) Science 252:809-17; Shi and Berg (1995) Chem. Biol. 2:83-9. These amino acids can be changed, while maintaining the remaining amino acids as a consensus backbone, to generate ZFPs with different and/or novel sequence specificities. See, e.g., Choo and Klug (1994) Proc. Natl. Acad. Sci. USA 91:11163-7; Desjarlais and Berg (1992) Proc. Natl. Acad. Sci. USA 89:7345-9; Desjarlais and Berg (1993) Proc. Natl. Acad. Sci. USA 90:2256-60; Greisman and Pabo (1997) Science 275:657-61; Isalan et al. (1998) Biochemistry 37:12026-33; Jamieson et al. (1994) Biochemistry 33:5689-95; Rebar and Pabo (1994) Science 263:671-3; Segal et al. (1999) Proc. Natl. Acad. Sci. USA 96:2758-63; Wolfe et al. (1999) J. Mol. Biol. 285:1917-34; Wu et al. (1995) Proc. Natl. Acad. Sci. USA 92:344-8. Moreover, at least two 3-finger ZFNs with different sequence specificities can be designed, such that they collaborate to produce cleavage. Smith et al. (2000), supra.

Design and selection approaches for constructing a ZFN of the invention may begin by determining one or more appropriate ZF motifs to recognize a specific nucleic acid sequence. Alternatively, a ZFN that recognizes a specific nucleic acid sequence may be used to construct a nucleic acid molecule comprising the specific nucleic acid sequence (e.g., wherein the specific nucleic acid sequence flanks a gene of interest) and other elements as needed. Design and various selection approaches for ZFPs, including the phage display method, have been reviewed. Mani et al. (2005), supra; Durai et al. (2005) Nucleic Acids Res. 33:5978-90; Isalan et al. (2001) Nat. Biotechnol. 19:656-60; Kandavelou et al. (2005) Nat. Biotechnol. 23:686-87; Pabo et al. (2001) Annu. Rev. Biochem. 70:313-40; Segal et al. (2003) Biochemistry 42:2137-48. Any design and/or selection approach known in the art may be used to arrive at a ZFN for use in embodiments of the present invention. For example, cell-based selection strategies using bacterial one-hybrid and two-hybrid systems may be used to produce highly specific ZFPs. Durai et al. (2006) Comb. Chem. High Throughput Screen. 9:301-11; Hurt et al. (2003) Proc. Natl. Acad. Sci. USA 100:12271-6; Joung et al. (2000) Proc. Natl. Acad. Sci. USA 97:7382-7. Highly specific ZFPs can also be obtained by directed domain shuffling and cell-based selection, which offers a general approach for optimizing multi-finger ZFPs. Hurt et al. (2003), supra.

A wealth of data based on design and phage display methodologies is available for ZF modules that specifically recognize 5' GNN 3' and 5' ANN 3' triplets, and to a lesser extent, the ZF motif preferences for 5' CNN 3' and 5' TNN 3' triplets are known. See, e.g., Durai et al. (2005), supra; Dreier et al. (2001) *J. Biol. Chem.* 276:29466-78; Dreier et al. (2005) *J. Biol. Chem.* 280:35588-97; Dreier et al. (2000) *J. Mol. Biol.* 303:489-502; Liu et al. (2002) *J. Biol. Chem.* 277:3850-6. Currently, two Web-based ZF design software packages are available (e.g., at zincfingertools.org). The foregoing renders nearly all genes encoded in a genome amenable to ZFN-mediated gene targeting. Katada and Komiyama (2009) *Chembiochem.* 10(8):1279-88.

In particular embodiments, a ZFN is used that binds the HIV co-receptor CCR5. Perez et al. (2008) *Nat. Biotechnol.* 26:808-16. This ZFN is termed the "CCR5ZFN." In particular embodiments, the CCR5ZFN coding region comprises: the opaque-2 nuclear localization sequence (Maddaloni et al. (1989) *Nucleic Acids Res.* 17(18):7532); the r162y11 zinc finger binding domain, the FokI nuclease domain (Looney et al. (1989) *Gene* 80:193-208); a T2A stutter sequence (Mattion et al. (1996) *J. Virol.* 70:8124-7) derived from the Thesoa assigna virus; a second opaque-2 nuclear localization sequence, the 168FA vE zinc finger binding domain; and a second FokI nuclease domain.

Nucleic Acid Molecules

In some embodiments, the method includes crossing a first plant having one or more genes of interest (which may confer a desirable trait or phenotype), such as two or more genes of interest, with a second plant. The second plant may also have one or more genes of interest. The first plant may include a vector, wherein the vector includes a promoter operably linked to one or more gene(s) of interest. The promoter may be a constitutive or inducible promoter. The nucleic acid sequence encoding a gene(s) of interest may be flanked by ZFN recognition sites. Optionally, the promoter operably linked to the gene(s) of interest, and any additional nucleic acid sequences (e.g., regulatory sequences), may also be flanked by ZFN recognition sites. The second plant may include another vector, which may include a tissue-specific or development-specific promoter operably linked to a nucleic acid sequence encoding a ZFN. The vectors may be stably integrated into the genomes of both plants. After crossing the first and second plants, the tissue-specific or development-specific promoter specifically drives the expression of the ZFN in the resulting progeny of such a cross. Expression of the ZFN in these progeny leads to excision of nucleic acid sequences flanked by the ZFN recognition sites, thereby reducing or eliminating the gene of interest, and optionally additional sequences (such as selectable marker genes) in specific tissues and/or stages of development of the progeny. In some embodiments, the ZFN recognition sites may be further flanked by homologous nucleic acid sequences to further promote homologous DNA recombination.

A gene of interest will typically be operably linked to one or more plant promoter(s) driving expression of the gene in an amount sufficient to confer a desired trait or phenotype. Promoters suitable for this and other uses are well known in the art. Non-limiting examples describing such promoters include U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (35S promoter); U.S. Pat. No. 6,433,252 (maize L3 oleosin promoter); U.S. Pat. No. 6,429,357 (rice actin 2 promoter, and rice actin 2 intron); U.S. Pat. No. 5,837,848 (root-specific promoter); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. patent application Ser. No. 09/757,089 (maize chloroplast aldolase promoter). Additional promoters include the nopaline synthase (NOS) promoter (Ebert et al. (1987) *Proc. Natl. Acad. Sci. USA* 84(16):5745-9); the octopine synthase (OCS) promoter (which is carried on tumor-inducing plasmids of *Agrobacterium tumefaciens*); the caulimovirus promoters such as the cauliflower mosaic virus (CaMV) 19S promoter (Lawton et al. (1987) *Plant Mol. Biol.* 9:315-24); the CaMV 35S promoter (Odell et al. (1985) *Nature* 313:810-2; the figwort mosaic virus 35S-promoter (Walker et al. (1987) *Proc. Natl. Acad. Sci. USA* 84(19):6624-8); the sucrose synthase promoter (Yang and Russell (1990) *Proc. Natl. Acad. Sci. USA* 87:4144-8); the R gene complex promoter (Chandler et al. (1989) *Plant Cell* 1:1175-83); the chlorophyll a/b binding protein gene promoter; CaMV35S (U.S. Pat. Nos. 5,322, 938, 5,352,605, 5,359,142, and 5,530,196); FMV35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank Accession No. V00087; Depicker et al. (1982) *J. Mol. Appl. Genet.* 1:561-73; Bevan et al. (1983) *Nature* 304:184-7), and the like.

Additional genetic elements that may optionally be operably linked to a gene of interest include sequences coding for transit peptides. For example, incorporation of a suitable chloroplast transit peptide, such as the *A. thaliana* EPSPS CTP (Klee et al. (1987) *Mol. Gen. Genet.* 210:437-42), and the *Petunia hybrida* EPSPS CTP (della-Cioppa et al. (1986) *Proc. Natl. Acad. Sci. USA* 83:6873-7) has been shown to target heterologous EPSPS protein sequences to chloroplasts in transgenic plants. Dicamba monooxygenase (DMO) may also be targeted to chloroplasts, as described in International PCT Publication No. WO 2008/105890.

Additional genetic elements that may optionally be operably linked to a gene of interest also include 5' UTRs located between a promoter sequence and a coding sequence that function as a translation leader sequence. The translation leader sequence is present in the fully processed mRNA upstream of the translation start sequence. The translation leader sequence may affect processing of the primary transcript to mRNA, mRNA stability, and/or translation efficiency. Examples of translation leader sequences include maize and petunia heat shock protein leaders (U.S. Pat. No. 5,362,865), plant virus coat protein leaders, plant rubisco leaders, and others. See, e.g., Turner and Foster (1995) *Molecular Biotech.* 3(3):225-36. Non-limiting examples of 5' UTRs include GmHsp (U.S. Pat. No. 5,659,122); PhDnaK (U.S. Pat. No. 5,362,865); AtAntl; TEV (Carrington and Freed (1990) *J. Virol.* 64:1590-7); and AGRtunos (GenBank Accession No. V00087; and Bevan et al. (1983) *Nature* 304:184-7).

Additional genetic elements that may optionally be operably linked to a gene of interest also include 3' non-translated sequences, 3' transcription termination regions, or poly-adenylation regions. These are genetic elements located downstream of a polynucleotide molecule, and include polynucleotides that provide polyadenylation signal, and/or other regulatory signals capable of affecting transcription, mRNA processing, or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA genes. A non-limiting example of a 3' transcription termination region is the nopaline synthase 3' region (nos 3'; Fraley et al. (1983) *Proc. Natl. Acad. Sci. USA* 80:4803-7). An example of the use of different 3' nontranslated regions is provided in Ingelbrecht et al., (1989) *Plant Cell* 1:671-80. Non-limiting examples of polyadenylation signals include one from a *Pisum sativum* RbcS2 gene (Ps.RbcS2-E9; Coruzzi et al. (1984) *EMBO J.* 3:1671-9) and AGRtu.nos (GenBank Accession No. E01312).

Plant Transformation

Any of the techniques known in the art for introduction of transgenes into plants may be used to produce a transformed plant according to the invention. Suitable methods for transformation of plants are believed to include virtually any method by which DNA can be introduced into a cell, such as: by electroporation as illustrated in U.S. Pat. No. 5,384,253; by microprojectile bombardment, as illustrated in U.S. Pat. Nos. 5,015,580, 5,550,318, 5,538,880, 6,160,208, 6,399,861, and 6,403,865; by *Agrobacterium*-mediated transformation as illustrated in U.S. Pat. Nos. 5,635,055, 5,824,877, 5,591,616; 5,981,840, and 6,384,301; and by protoplast transformation, as set forth in U.S. Pat. No. 5,508,184, etc. Through the application of techniques such as these, the cells of virtually any plant species may be stably transformed, and these cells may be developed into transgenic plants by techniques known to those of skill in the art. Techniques that may be particularly useful in the context of cotton transformation are disclosed in U.S. Pat. Nos. 5,846,797, 5,159,135, 5,004,863, and 6,624,344; techniques for transforming *Brassica* plants in particular are disclosed, for example, in U.S. Pat. No. 5,750,871; techniques for transforming soybean are disclosed, for example, in U.S. Pat. No. 6,384,301; and techniques for transforming corn are disclosed, for example, in U.S. Pat. No. 7,060,876, U.S. Pat. No. 5,591,616, and International PCT Publication WO 95/06722.

After effecting delivery of exogenous DNA to recipient cells, the next steps generally concern identifying the transformed cells for further culturing and plant regeneration. In order to improve the ability to identify transformants, one may desire to employ a selectable or screenable marker gene with the transformation vector used to generate the transformant. In this case, the potentially transformed cell population can be assayed by exposing the cells to a selective agent or agents, or the cells can be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a gene of interest (e.g., a transgene) in the regenerating plants, a variety of assays may be performed. Such assays include, for example: molecular biological assays, such as Southern and Northern blotting and PCR; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

Cultivation and Use of Transgenic Plants

A plant exhibiting nucleic acid excision according to the present invention may have one or more desirable traits, such as two or more desirable traits. Such traits can include, for example: resistance to insects and other pests and disease-causing agents; tolerances to herbicides; enhanced stability, yield, or shelf-life; environmental tolerances; pharmaceutical production; industrial product production; and nutritional enhancements. The desirable traits may be conferred by genes flanked by nucleic acid sequence recognized by ZFN(s) expressed in the plant exhibiting the desirable traits, such that expression of the ZFN(s) in the plant decreases or eliminates transmission of the trait, through containment of its underlying gene, to other plants or subsequent generations of the plant. Thus, in one embodiment, the desired trait can be due to the presence of a transgene(s) in the plant, which may be flanked by ZFN recognition sequences. In an additional embodiment, the desirable trait can be obtained through conventional breeding, which trait may be conferred by one or more genes flanked by ZFN recognition sequences.

A plant exhibiting nucleic acid excision according to the invention may be any plant capable of being transformed with a nucleic acid molecule of the invention. Accordingly, the plant may be a dicot or monocot. Non-limiting examples of dicotyledonous plants usable in the present methods include alfalfa, beans, broccoli, cabbage, carrot, cauliflower, celery, Chinese cabbage, cotton, cucumber, eggplant, lettuce, melon, pea, pepper, peanut, potato, pumpkin, radish, rapeseed, spinach, soybean, squash, sugarbeet, sunflower, tobacco, tomato, and watermelon. Non-limiting examples of monocotyledonous plants usable in the present methods include corn, onion, rice, sorghum, wheat, rye, millet, sugarcane, oat, triticale, switchgrass, and turfgrass.

Plants exhibiting nucleic acid excision according to the invention may be used or cultivated in any manner, wherein transmission of the excised nucleic acid sequence to other plants is undesirable. Accordingly, GM plants that have been engineered to, inter alia, have one or more desired traits, may be transformed with nucleic acid molecules according to the invention, and cropped and cultivated by any method known to those of skill in the art.

EXAMPLES

The following examples are included to illustrate embodiments of the invention. It will be appreciated by those of skill in the art that the techniques disclosed in the Examples represent techniques discovered by the inventors to function well in the practice of the invention. However, those of skill in the art will, in light of the present disclosure, can appreciate that many changes can be made in the specific embodiments which are disclosed and still obtain a like or similar result without departing from the scope of the invention. More specifically, it will be apparent that certain agents that are both chemically and physiologically related may be substituted for the agents described herein, while the same or similar results would be achieved. All such similar substitutes and modifications apparent to those skilled in the art are deemed to be within the scope of the invention as defined by the appended Claims.

Example I: Plasmid Design and Construction

A target construct containing a target reporter gene expression cassette flanked by zinc finger binding sites (pDAS5380) and an excision construct containing a zinc finger nuclease gene expression cassette (pDAS5381) were designed and constructed. The constructs were designed to be transformed separately into tobacco. Target reporter gene excision was carried out by crossing the two tobacco lines, wherein a functional zinc finger nuclease recognized the zinc finger binding sites flanking the target reporter gene cassette and cleaved the genomic DNA. Crossing the plant lines containing the target reporter gene construct with the plant line containing the excision construct resulted in the removal/deletion of the reporter gene from the plant genome.

Construction and Design of Target Construct pDAS5380.

pDAS5380 (FIG. 1) was constructed as a binary plasmid vector. This construct contains the following plant transcription unit (PTU) expression cassettes and genetic elements: RB7 MAR ((Matrix Attachment Region (Thompson et al. (1997) WO9727207))::CCR5 binding site repeated 4× (Perez et al. (2008) Nat. Biotechnol. 26:808-16)::AtuORF1 3' UTR (Agrobacterium tumefaciens open reading frame-1, 3' untranslated region (Huang et al. (1990) J. Bacteriol. 172:1814-22))/GUS (β-D-glucuronidase (Jefferson (1989) Nature 342:837-8))/AtUbi10 (Arabidopsis thaliana ubiquitin-10 promoter (Callis et al. (1990) J. Biol. Chem. 265: 12486-93))::CCR5Binding Site repeated 4x::AtAct2 (A. thaliana actin-2 promoter (An et al. (1996) Plant J. 10:107-21))/Turbo GFP (turbo-green fluorescence protein (Evdokimov et al. (2006) EMBO Rep. 7(10):1006-12))/Atu ORF23 3' UTR (A. tumefaciens open reading frame-23, 3' untranslated region (Gelvin et al. (1987) EP222493))::AtUbi10/PAT (phosphinothricin acetyl transferase (Wohlleben et al. (1988) Gene 70:25-37))/Atu ORF1 3' UTR. The GUS PTU expression cassette was placed in trans to the GFP and PAT PTU expression cassettes. In addition, the GUS PTU expression cassette was flanked by CCR5 zinc finger nuclease binding sites. This sequence (SEQ ID NO:1) was repeated 4× directly upstream and downstream of the GUS PTU expression cassette. The locations of the zinc finger binding sites are identified in FIG. 1 as "CCR5 BINDING SITE." These sites are recognized and bound by the zinc finger nuclease protein encoded by excisor construct, pDAS5381. The assembly of this binary vector was completed using standard molecular biology techniques. The final plasmid was confirmed via restriction enzyme digestion and DNA sequencing.

Construction and Design of Excisor Construct, pDAS5381.

Figure 2:
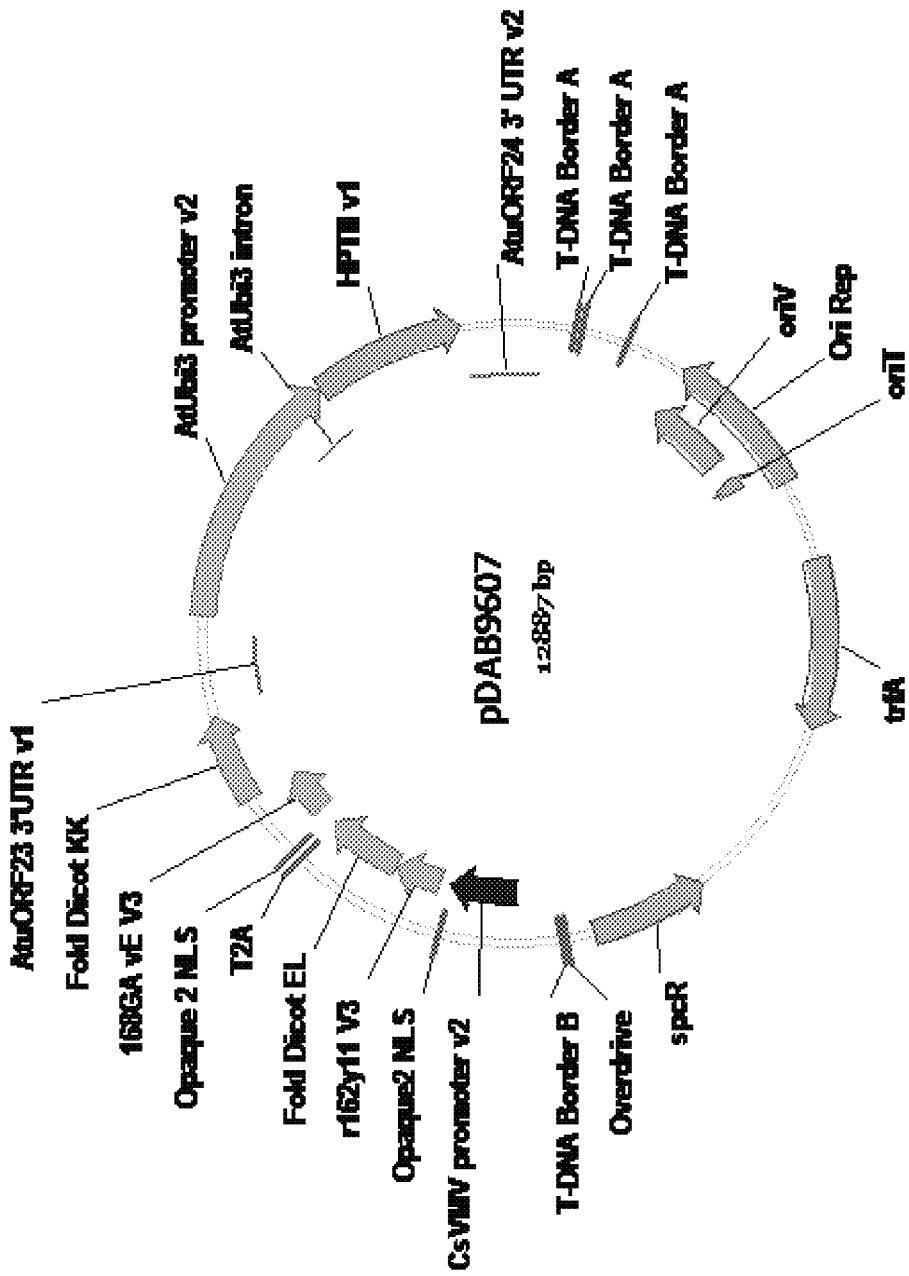
FIG. 2 includes the plasmid map for plasmid pDAS5381.

A binary plasmid containing a zinc finger nuclease gene that was specifically designed to bind the CCR5 binding site (SEQ ID NO:2) was designed and constructed as described in Perez et al., (2008) Nature Biotechnol. 26:808-16. pDAS5381 (FIG. 2) contains the following PTU expression cassettes: CsVMV (Cassava Vein Mosaic Virus promoter (Verdaguer et al. (1996) Plant Mol. Biol. 31:1129-39))/CCR5 zinc finger nuclease coding region (containing: the opaque-2 nuclear localization sequence (Maddaloni et al. (1989) Nucleic Acids Res. 17(18):7532); the r162y11 zinc finger binding domain; the Fold nuclease domain (Looney et al. (1989) Gene 80:193-208); a T2A stutter sequence (Mattion et al. (1996) J. Virol. 70:8124-7) derived from the Thesoa assigna virus; a second opaque-2 nuclear localization sequence; the 168GA vE zinc finger binding domain; and a second Fold nuclease domain)/Atu ORF23 3' UTR:: AtUbi3 promoter (A. thaliana ubiquitin-3 promoter (Callis et al. (1995) Genetics 139(2):921-39))/HPTII (hygromycin phosphotransferase II (Gritz et al. (1983) Gene 25(2-3):179-88))/Atu ORF24 3' UTR (A. tumefaciens open reading frame-24, 3' untranslated region (Gelvin et al. (1987) EP222493)). The assembly of this binary vector was completed using standard molecular biology techniques. The final plasmid was confirmed via restriction enzyme digestion and DNA sequencing.

Example II: Agrobacterium-Mediated Plant Transformation

Transformation of Agrobacterium with pDAS5380 and pDAS5381.

Electrocompetent A. tumefaciens (strain LBA4404) cells were obtained from Invitrogen (Carlsbad, Calif.) and transformed using an electroporation method adapted from Weigel and Glazebrook (2002) "How to Transform Arabidopsis," in Arabidopsis: A Laboratory Manual, Cold Spring Harbor Laboratory Press, Cold Spring Harbor, N.Y., U.S.A. Transformed colonies were obtained on yeast extract peptone media (YEP) containing spectinomycin (50 µg/mL) and streptomycin (125 µg/mL) and confirmed via restriction enzyme digestion. Clones which exhibited the correct restriction enzyme banding patterns were stored as glycerol stocks at −80° C.

Agrobacterium-Mediated Transformation of Nicotiana tabacum.

Tobacco (cv. Petit Havana) leaf discs were transformed using A. tumefaciens (strain LBA4404) containing pDAS5381 and pDAS5380. Single colonies of Agrobacterium containing these plasmids were inoculated into 4 mL of YEP containing spectinomycin (50 µg/mL) and streptomycin (125 µg/mL) and incubated overnight at 28° C. on a shaker at 190 rpm. The 4 mL seed culture was subsequently used to inoculate a 25 mL culture of YEP media containing spectinomycin (50 µg/mL) and streptomycin (125 µg/mL) grown in a 125 mL baffled Erlenmeyer flask. This culture was incubated at 28° C. shaking at 190 rpm until it reached an $OD_{600}$ of ~1.2. Ten mL of Agrobacterium suspension was placed into sterile 60×20 mm Petri dishes.

Twenty-five freshly cut leaf discs (0.5 cm$^2$) cut from plants aseptically grown on MS medium (Phytotechnology Labs, Shawnee Mission, Kans., #M524) with 30 g/L sucrose in PhytaTrays™ (Sigma, St. Louis, Mo.) were soaked in 10 mL of overnight culture of Agrobacterium for a few minutes, blotted dry on sterile filter paper, and then placed onto the same medium with the addition of 1 mg/L indoleacetic acid and 1 mg/L benzyamino purine. Following 48 hours of co-cultivation, leaf discs co-cultivated with Agrobacterium harboring pDAS5380 were transferred to the same medium with 5 mg/L Basta® and 250 mg/L cephotaxime. Leaf discs co-cultivated with Agrobacterium harboring pDAS5381 were transferred to the same medium with 10 mg/L hygromycin and 250 mg/L cephotaxime. After 3 weeks, individual $T_0$ plantlets were transferred to either MS medium with 10 mg/L Basta® and 250 mg/L cephotaxime for pDAS5380, or with 10 mg/L hygromycin and 250 mg/L cephotaxime for pDAS5381, an additional 3 weeks prior to transplanting to soil and transfer to the greenhouse.

Copy Number, Full Length PTU and Expression Analysis of T$_0$ Plants.

Copy Number Assay.

Invader® and hydrolysis probe assays were performed to screen samples of Basta®-resistant plants to identify those that contained single copy integration of the T-DNA in pDAS5380 and pDAS5381. Detailed analysis was conducted using primers and probes specific to gene expression cassettes. Single copy events were identified for additional analysis.

Tissue samples were collected in 96-well plates and lyophilized for 2 days. Tissue maceration was performed with a Kleco™ tissue pulverizer and tungsten beads (Visalia, Calif.). Following tissue maceration, the genomic DNA was isolated in high-throughput format using the DNeasy 96 Plant Kit™ (Qiagen, Germantown, Md.) according to the manufacturer's suggested protocol. Genomic DNA was quantified by Quant-IT Pico Green DNA assay Kit™ (Molecular Probes, Invitrogen, Carlsbad, Calif.). Quantified genomic DNA was adjusted to 9 ng/µL for the Invader® assay or to 5 ng/µL for the hydrolysis probe assay using a Biorobot3000™ automated liquid handler (Qiagen, Germantown, Md.).

Custom Invader® assays were developed for PAT gene analysis in tobacco by Hologic (Madison, Wis.). The genomic DNA samples (7.5 µL at 9 ng/µL) were first denatured in 96-well plate format by incubation at 95° C. for 10 minutes and then cooled on ice. Next, 7.5 µL of master mix (3 µL of probe mix for pat and an internal reference gene (phenylalanine ammonium lyase (palA); GenBank ID: AB008199), 3.5 µL Cleavase® XI FRET mix, and 1 µL of Cleavase® XI Enzyme/MgCl$_2$ solution) were added to each well and the samples were overlaid with mineral oil. Plates were sealed and incubated at 63° C. for 1 hour in a BioRad Tetrad® thermocycler. Plates were cooled to ambient temperature before being read on a fluorescence plate reader. All plates contained 1 copy, 2 copy and 4 copy standards as well as wild-type control samples and blank wells containing no sample. Readings were collected for both FAM (λ 485-528 nm) and RED (λ 560-620 nm) channels, and from these the fold over zero (i.e., background) for each channel was determined for each sample by the sample raw signal divided by no template raw signal. From this data, a standard curve was constructed and the best fit determined by linear regression analysis. Using the parameters identified from this fit, the apparent pat copy number was then estimated for each sample.

Transgene copy number determination by hydrolysis probe assay, analogous to TaqMan® assay, was performed by real-time PCR using the LightCycler® 480 system (Roche Applied Science, Indianapolis, Ind.). Assays were designed for HPTII, PAT and the internal reference gene phenylalanine ammonium lyase (palA) using LightCycler® Probe Design Software 2.0. For amplification, LightCycler® 480 Probes Master mix (Roche Applied Science, Indianapolis, Ind.) was prepared at 1× final concentration in a 10 µL volume multiplex reaction containing 0.4 µM of each primer and 0.2 µM of each probe (Table 1). A two-step amplification reaction was performed with an extension at 58° C. for 38 seconds with fluorescence acquisition. All samples were run in triplicate and the averaged Cycle threshold (Ct) values were used for analysis of each sample. Analysis of real-time PCR data was performed using LightCycler® software release 1.5 using the relative quant module and is based on the ΔΔCt method. For this, a sample of genomic DNA from a single copy calibrator and known 2 copy check were included in each run (identical to those used for Invader® assays above).

TABLE 1

Primer and probe Information for hydrolysis probe assay of PAT, HPTII, and internal reference (palA).

| Primer Name | Sequence | Detection |
|---|---|---|
| TQPATS | SEQ ID NO: 3; 5' ACAAGAGTGGATTG ATGATCTAGAGAGGT 3' | |
| TQPATA | SEQ ID NO: 4; 5' CTTTGATGCCTATG TGACACGTAAACAGT 3' | |
| TQPATFQ | SEQ ID NO: 5; 5' CY5-GGTGTTGTGG CTGGTATTGCTTACGCTGG-BHQ2 3' | Cy5 |
| TQPALS | SEQ ID NO: 6; 5' TACTATGACTTGAT GTTGTGTGGTGACTGA 3' | |
| TQPALA | SEQ ID NO: 7; 5' GAGCGGTCTAAATT CCGACCCTTATTTC 3' | |
| TQPALFQ | SEQ ID NO: 8; 5' 6FAM-AAACGATGG CAGGAGTGCCCTTTTTCTATCAAT-BHQ1 3' | 6FAM |
| HPT2S | SEQ ID NO: 9; 5' ACACTACATGGCGT GATTT 3' | |
| HPT2A | SEQ ID NO: 10; 5' AGCATCAGCTCAT CGAGA 3' | |
| HPTFQ | SEQ ID NO: 11; 5' Cy5/ACTGTGAT GGACGACACCG/3BHQ2/3' | Cy5 |

Full Length PTU Assay Via Southern Blot Analysis.

Southern blot analysis was used to establish the integration pattern of the inserted DNA fragment and identify pDAS5380 and pDAS5381 events which contained a full length PTU. Data were generated to demonstrate the integration and integrity of the transgenes inserted into the tobacco genome. Southern blot data was used to identify simple integration of an intact copy of the T-DNA from pDAS5380 and pDAS5381. Detailed Southern blot analysis was conducted using probes specific to gene expression cassettes. The hybridization of these probes with genomic DNA that had been digested with specific restriction enzymes identified genomic DNA fragments of molecular weights, the patterns of which could be analyzed to identify events for advancement to T$_1$. These analyses also showed that the plasmid fragment had been inserted into tobacco genomic DNA without rearrangements of the PTU.

Tissue samples were collected in 50 mL conical tubes (Fisher Scientific, Pittsburgh, Pa.) and lyophilized for 2 days. Tissue maceration was performed with a paint mixer tissue pulverizer and tungsten beads. Following tissue maceration, the genomic DNA was isolated using the DNeasy™ Plant Maxi Kit (Qiagen, Germantown, Md.) according to manufacturer suggested protocol. Purified genomic DNA was precipitated and resuspended in 500 µL TE buffer. The genomic DNA was further purified using the Qiagen Genomic Tips™ kit. Genomic DNA was quantified by Quant-IT Pico Green™ DNA assay kit (Molecular Probes, Invitrogen, Carlsbad, Calif.). Quantified genomic DNA was adjusted to 8 µg in a consistent volume.

For each sample, 8 µg of genomic DNA was thoroughly digested with the restriction enzymes MfeI and NsiI (New England Biolabs, Beverley, Mass.). Samples were incubated at 37° C. overnight. The digested DNA was concentrated by precipitation with Quick Precipitation Solution™ (Edge Biosystems, Gaithersburg, Md.) according to the manufacturer's suggested protocol. The genomic DNA was then resuspended in 25 μL of water at 65° C. for 1 hour. Resuspended samples were loaded onto a 0.8% agarose gel prepared in 1×TAE and electrophoresed overnight at 1.1 V/cm in 1×TAE buffer. The gel was sequentially subjected to denaturation (0.2 M NaOH/0.6 M NaCl) for 30 minutes, and neutralization (0.5 M Tris-HCl (pH 7.5)/1.5 M NaCl) for 30 minutes.

Transfer of DNA fragments was performed by passively wicking 20×SSC solutions overnight through the gel onto treated Immobilon™ NY+transfer membrane (Millipore, Billerica, Mass.) by using a chromatography paper wick and paper towels. Following transfer, the membrane was briefly washed with 2×SSC, cross-linked with the Stratalinker™ 1800 (Stratagene, LaJolla, Calif.), and vacuum baked at 80° C. for 3 hours.

Blots were incubated with pre-hybridization solution (Perfect Hyb Plus™, Sigma, St. Louis, Mo.) for 1 hour at 65° C. in glass roller bottles using a model 400 hybridization incubator (Robbins Scientific, Sunnyvale, Calif.). Probes were prepared from a PCR fragment containing the entire coding sequence. The PCR amplicon was purified using QIAEX II™ gel extraction kit and labeled with $\alpha^{32}$P-dCTP via the Random RT Prime IT™ labeling kit (Stratagene, La Jolla, Calif.). Blots were hybridized overnight at 65° C. with denatured probe added directly to hybridization buffer to approximately 2 million counts per blot per mL. Following hybridization, blots were sequentially washed at 65° C. with 0.1×SSC/0.1% SDS for 40 minutes. Finally, the blots were exposed to chemiluminescent film (Roche Diagnostics, Indianapolis, Ind.) and imaged using a Molecular Dynamics Storm 860™ imaging system.

Figure 3A:
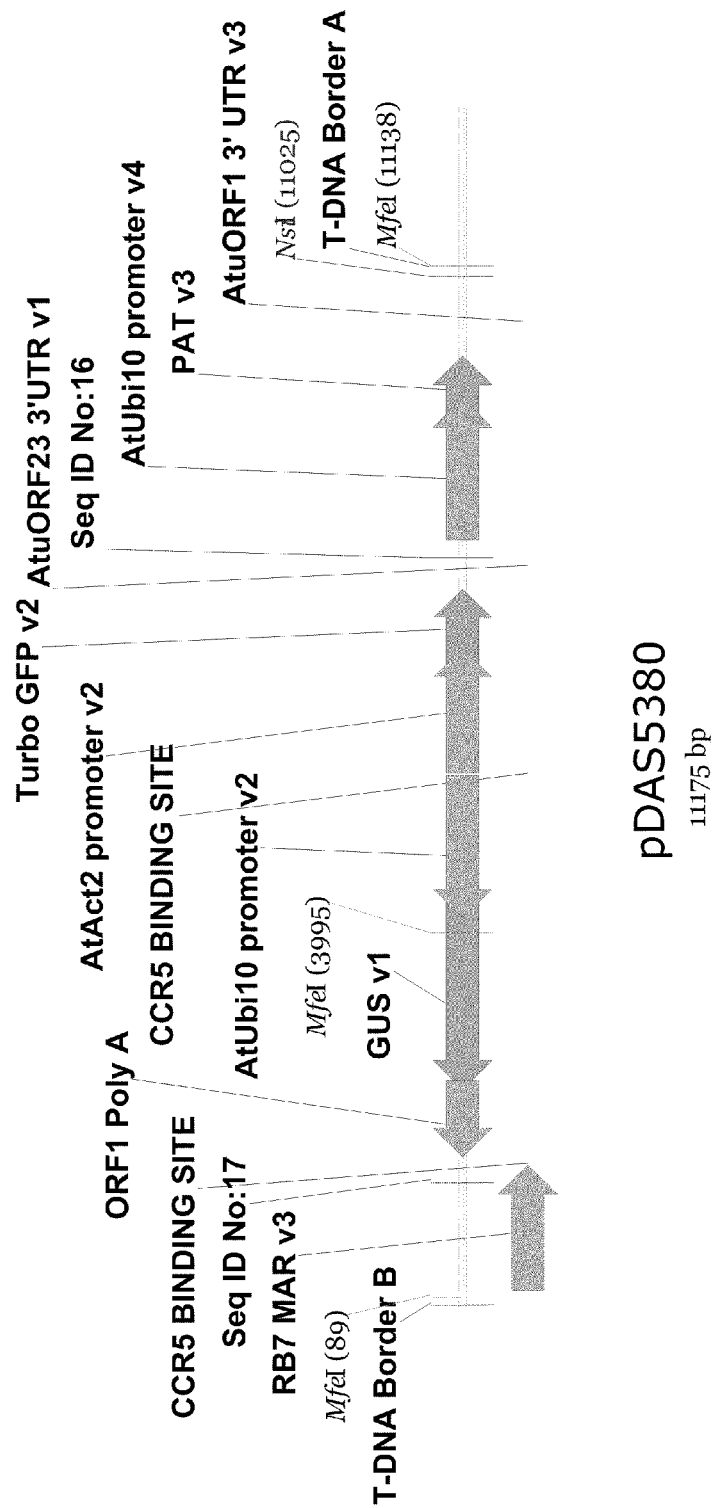
FIG. 3a is a schematic diagram and restriction map of the T-DNA insert.
Figure 3B:
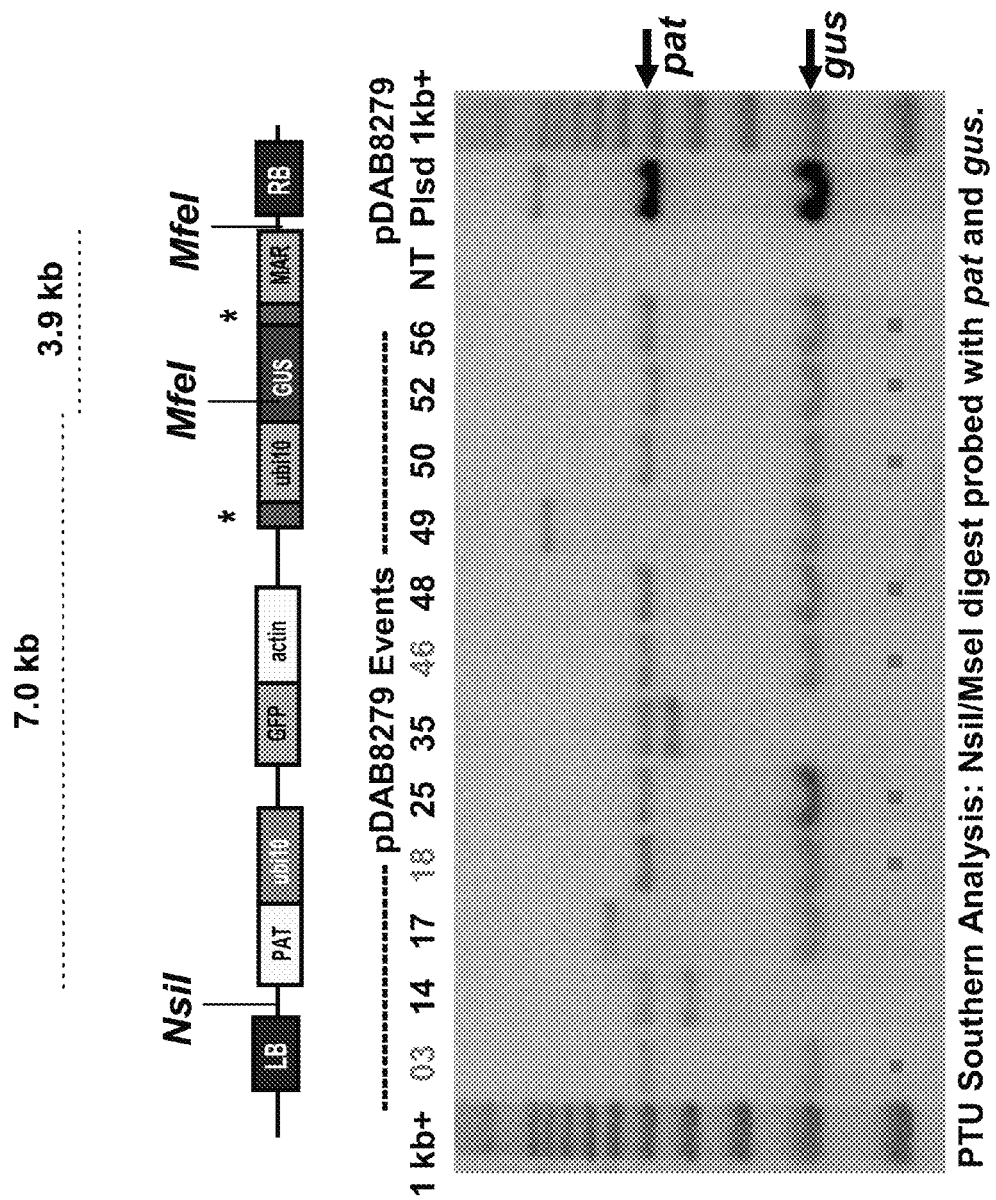
FIG. 3b includes several panels depicting $T_0$ Southern blot analysis used to identify events which contained full length intact PTUs from plasmid pDAS5380 according to an embodiment of the invention. The $T_0$ Southern blot analysis image used restriction enzymes MfeI and NsiI to digest the pDAS5380 events, showing intact T-DNA inserts by co-hybridization of GUS and PAT.
Figure 4A:
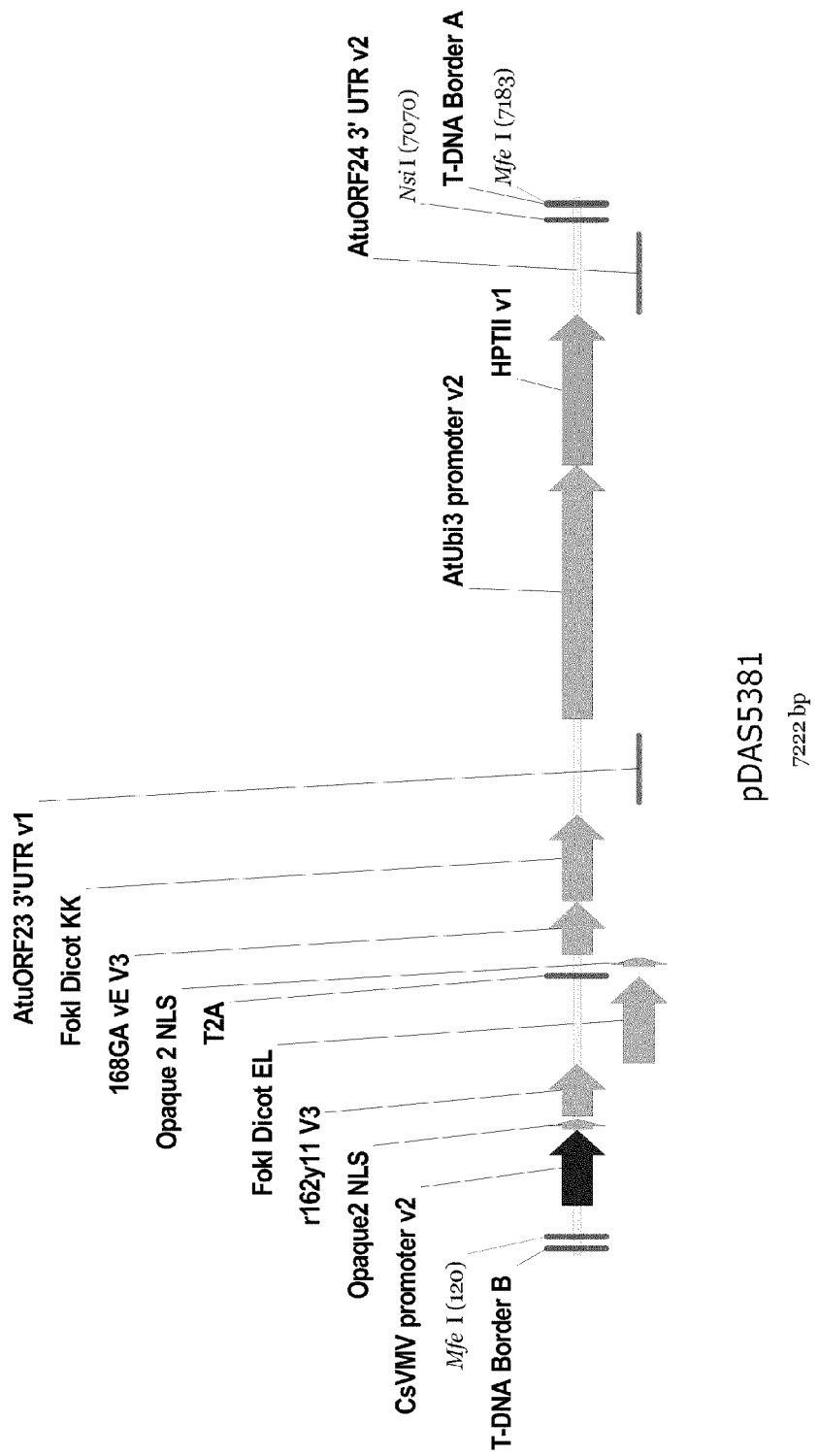
FIG. 4A is a schematic diagram and restriction map of the T-DNA insert.
Figure 4B:
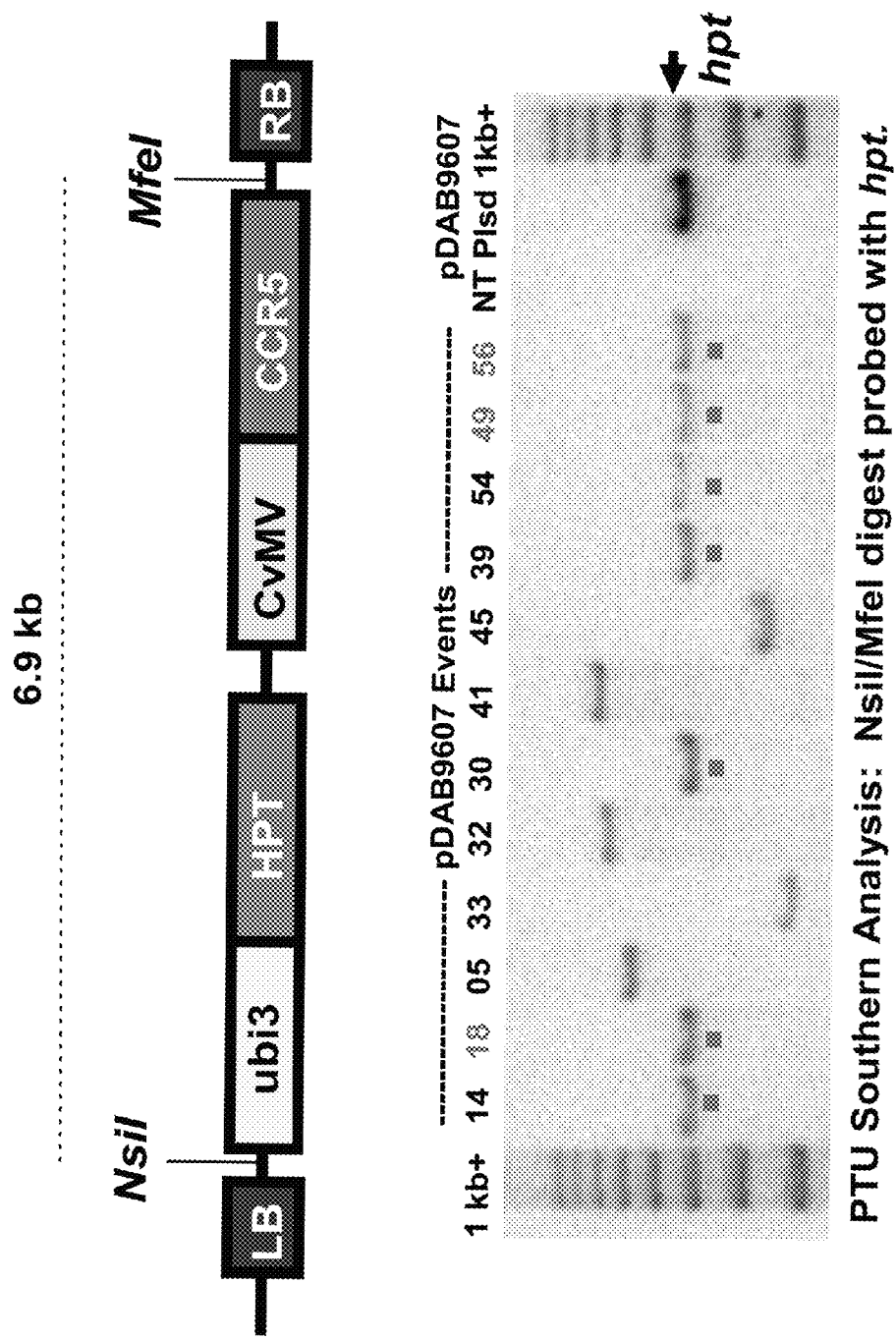
FIG. 4b includes several panels depicting $T_0$ Southern blot analysis used to identify events which contained full length intact PTUs from plasmid pDAS5381 according to an embodiment of the invention. The $T_0$ Southern blot analysis image used restriction enzymes MfeI and NsiI to digest the pDAS5381 events, showing intact T-DNA inserts by hybridization of HptII.

Expected and observed fragment sizes with a particular digest and probe, based on the known restriction enzyme sites of the pDAS5380 or pDAS5381 fragment, are indicated in FIGS. 3 and 4. The Southern blot analyses completed in this study were used to identify events that contained full-length intact PTUs from plasmids pDAS5380 or pDAS5381 that were inserted into the tobacco genome (FIGS. 3 and 4, respectively).

GUS Expression Assay.

To test whether the pDAS5380 transgenic plants contained a functional GUS PTU expression cassette, leaf samples were harvested and stained histochemically for GUS expression. Leaf discs (~0.25 cm$^2$) were cut and placed in a 24-well tray (1 leaf disc per well) containing 250 μL of GUS assay solution (Jefferson (1989) Nature 342:837-8). The 24-well dish was wrapped with Nescofilm® (Fisher Scientific, Pittsburgh, Pa.) and incubated at 37° C. for 24 hours. After 24 hours, the GUS assay solution was removed from each well and replaced with 250 μL of 100% ethanol. The dish was wrapped with Nescofilm® and incubated at room temperature for 2-3 hours. The ethanol was removed and replaced with fresh ethanol. The leaf discs were then viewed under a dissecting microscope. Leaf discs which were stained blue were scored as containing a functional GUS PTU expression cassette.

GFP Expression Assay.

Tobacco leaf samples were analyzed for GFP expression using ELISA. Plates were coated with a purified rabbit anti-GFP antibody overnight at 4° C. The day of analysis, plates were blocked with 0.5% BSA in PBST. Duplicated leaf samples were extracted by bead beating frozen leaf pieces with 2 stainless steel beads in a Kleco™ tissue grinder for 3 minutes at maximum speed. The samples were centrifuged at 3000 rcf for 10 minutes and the supernatants collected. Extract samples were loaded onto ELISA plates at 1:5 and 1:50 dilutions. An *E. coli* recombinant GFP standard curve was run on each plate with concentrations from 12.5 ng/mL to 0.195 ng/mL. The standards and samples were incubated on the ELISA plates for 1 hour. Plates were washed and a horseradish peroxidase conjugated rabbit anti-GFP antibody was added. Following 1 hour incubation, the plates were washed and substrate was added. Color was allowed to develop before stopping the reaction with $H_2SO_4$. Absorbance was read on a plate reader at 450 nm with a 650 nm reference filter. A quadratic standard curve was generated by fitting concentration of the *E. coli* standard against OD. Concentrations of unknown samples were determined by linear regression.

Selection of $T_0$ Plants for Target $T_1$ Production.

A total of 68 Basta®-resistant, GUS+/GFP+ plants were regenerated and 38 plants were found to have 1-2 transgene copies based on PAT Invader® assay. Southern analysis identified 14 single-copy events, of which 8 displayed bands consistent with intact PAT, GUS and GFP PTUs. Three pDAS5380 events displaying single copy, full length PTU, and expressing GUS and GFP, pDAS5380-3, pDAS5380-18 and pDAS5380-46, were self-pollination to produce $T_1$ seed.

Fold Expression Assay.

Quantitative Real-Time PCR (qRT-PCR) was used to quantify the mRNA expression of the zinc finger nuclease in $T_0$ tobacco plants transformed with pDAS5381. The assay was developed to quantify the relative Fold mRNA expression from tobacco leaf samples by normalizing these levels against mRNA expression from input mRNA. The normalization of the FokI mRNA against total mRNA permits comparison of FokI expression between different samples, and can be used to identify events that appear to be highly expressing. The relative ZFN expression is listed in Table 1.1.

TABLE 1.1

Quantification of mRNA expression of the zinc finger nuclease in $T_0$ tobacco plants transformed with pDAS5381.

| T0 Event | Relative ZFN Expression* | Standard Deviation | % CV |
|---|---|---|---|
| pDAS5381-14 | 3.21 | 1.56 | 36.0 |
| pDAS5381-18 | 41.30 | 1.56 | 3.8 |
| pDAS5381-30 | 8.39 | 0.86 | 10.3 |
| pDAS5381-39 | 17.70 | 1.92 | 10.8 |
| pDAS5381-49 | 47.55 | 1.79 | 3.8 |
| pDAS5381-54 | 4.45 | 0.57 | 12.8 |
| pDAS5381-56 | 11.73 | 2.5 | 21.3 |

*qRT-PCR for Fok1 mRNA normalized to total RNA. Mean of 4 replicate samples.

Leaf material from $T_0$ tobacco plants that had been transformed with pDAS5381 was collected and placed on ice. Total RNA was isolated using Qiagen's RNeasy® Plant Mini Kit (Qiagen, Germantown, Md.). Total mRNA was treated with RNase-free DNase per the manufacturer's recommendation to remove any contaminating DNA that might amplify during quantitative RT-PCR. First strand synthesis was set up according to the Superscript III™ Reverse Transcriptase Enzyme (Invitrogen, Carlsbad, Calif.) manufacturer's instructions and primed using random hexamers. The synthesized cDNA strands were diluted in water at ratios of 1:10 and 1:50. Each aliquot was stored at −20° C.

The qRT-PCR reaction was completed as follows: forward primer Fok1_UPL_F (SEQ ID NO:12), reverse primer Fok1_UPL_R (SEQ ID NO:13), probe UPL #130 (cat

04693663001, Roche, Indianapolis, Ind.), 1× LC480 Probes Master Buffer (Roche Diagnostic, Indianapolis, Ind.), and 1.5 µL of synthesized cDNA in a 15 µL reaction. Serial dilutions of the synthesized cDNA were made and assayed in repetition. The cocktail was amplified using LightCycler® 480 Probes Master kit #04707494001 (Roche Diagnostics, Indianapolis, Ind.). A 96-well microplate was demarcated and labeled, 13.5 µL of master mix was added per well. A sealing foil was gently attached to the microplate. The plate was centrifuged for 1 minute at 3,000 rpm in a Qiagen microplate centrifuge. The sealing foil was removed and 1.5 µL of thawed, diluted synthesized cDNA strands were added. A foil seal was firmly affixed to the plate and centrifuged as previously described. A PCR program was run as follows: i) activate 95° C. for 5 minutes; ii) denature 95° C. for 10 sec (@ 4.8° C./sec); iii) anneal/extend 60° C. for 25 sec (@ 2.5° C./sec); iv) acquire 72° C. for 1 sec (@ 4.8° C./sec); steps ii-iv were repeated 45 more times; vi) cool to 38° C. for 5 sec.

A qRT-PCR assay for quantifying the mRNA expression of the internal reference gene was completed as another method to normalize the zinc finger nuclease mRNA expression. The actin qRT-PCR reaction was completed as follows: forward primer BY2ACT89S (SEQ ID NO:14), reverse primer BY2ACTFQ (SEQ ID NO:15), probe BYACTFQ (SEQ ID NO:18), 1×LC480 Probes Master Buffer, and 2.0 µL of synthesized cDNA, in a 10 µL reaction. Serial dilutions of the synthesized cDNA were made and assayed in repetition. In addition, 2 µL of plasmid DNA copy number standards were added to separate wells in a dilution series from lowest to highest concentrations, and these standards were compared to the actin cDNA (synthesized from total mRNA) to quantify the copy number. Actin DNA copy number standard series were made by cloning the target amplicon into a pCR2.1 plasmid (Invitrogen, Carlsbad, Calif.), and making a dilution series, prepared in dilution buffer (10 mM Tris-HCl [pH 8.0], 100 µg/mL yeast tRNA), for quantifying the copy number. The cocktail was amplified using LightCycler® 480 Probes Master kit #04707494001 (Roche Diagnostics, USA). A 96-well microplate was demarcated and labeled, and 8.0 µL, of master mix was added per well. A sealing foil was gently attached to the microplate. The plate was centrifuged for 1 minute at 3,000 rpm in a Qiagen microplate centrifuge. The sealing foil was removed, and 2.0 µL, of thawed, diluted synthesized cDNA strands or plasmid DNA were added. A foil seal was firmly affixed to the plate and centrifuged as previously described. A PCR program was run as follows: i) activate 95° C. for 10 minutes; ii) denature 95° C. for 10 sec (@ 4.8° C./sec); iii) anneal/extend 56° C. for 40 sec (@ 2.5° C./sec); iv) acquire 72° C. for 1 sec (@ 4.8° C./sec); steps ii-iv were repeated 45 more times; vi) cool to 38° C. for 5 sec.

Selection of $T_0$ Plants for Excisor $T_1$ Production.

A total of 54 hygromycin-resistant plants were regenerated, and 34 plants were found to have 1-2 transgene copies based on hydrolysis probe assay. Southern analysis identified 12 single-copy events of which 7 displayed bands consistent with intact HPT and ZFN PTUs. $T_0$ pDAS5381 events displaying single copy transgene, full length PTU, and expressing Fok1, pDAS5381-18, pDAS5381-49 and pDAS5381-56, were self-pollination to produce $T_1$ seed.

Example III: Generation and Selection of $T_1$ Plants

Selfing of $T_0$ Plants to Produce Homozygous $T_1$ Plants.
The following $T_0$ plant events: pDAS5380-3; pDAS5380-18; pDAS5380-46; pDAS5381-18; pDAS5381-49; and pDAS5381-56 were grown to maturity and self-fertilized to produce $T_1$ seed. Following germination, $T_1$ plants that were homozygous for the pDAS5380 and pDAS5381 constructs were used for transgene deletion. According to Mendelian inheritance, crossing the pDAS5381 homozygous single copy $T_1$ plants with the pDAS5380 homozygous single copy $T_1$ plants produce an $F_1$ population containing a heterozygous single copy of both the pDAS5381 and pDAS5380 constructs. The progeny of this cross was expected to contain one copy of the GUS reporter gene. As such, an $F_1$ plant not expressing GUS indicates that the GUS PTU expression cassette has been excised.

$T_0$ plants were grown under a 16:8-hour photoperiod, with daytime and nighttime temperature between 22-24° C. When the primary flowering stem began to elongate and form flower buds, the entire plant was covered with a selfing bag to prevent outcrossing. Seeds derived from self-pollination were harvested about eight weeks after transplanting. The seed from the self-fertilized plants was collected and sewn into soil. The resulting $T_1$ populations were grown in the greenhouse under the conditions described above.

Molecular Screening of $T_1$ Plants.

Zygosity Assay.

An assay to quantify the zygosity of the $T_1$ plants was completed using the hydrolysis probe method described, supra (Copy Number Assay). The analysis of real time PCR data was performed and the number of transgene copies contained in the $T_1$ plants was determined by comparison to a copy number control. For this, a sample of genomic DNA from the parent $T_0$ plant which was previously shown to contain a single copy calibrator was included. Homozygous pDAS5380 and pDAS5381 $T_1$ plants were identified.

GUS Expression Assay.

It was important to identify expressing events for advancement to the crossing experiments. The pDAS5380 $T_1$ plants were assayed using the protocol described, supra (GUS Expression Assay). The pDAS5380 plants which were selected as homozygous for the pDAS5380 construct from the zygosity assay, supra, were tested. All of the plants stained blue.

GFP Expression Assay.

The pDAS5380 $T_1$ plants were assayed using the protocol described, supra (GFP Expression Assay). The pDAS5380 plants which were selected as homozygous for the pDAS5380 construct from the zygosity assay, supra, were tested. All of the tested plants were positive for GFP expression.

Fold Expression Assay.

Quantitative Real-Time PCR (qRT-PCR) was used to quantify the mRNA expression of the zinc finger nuclease in homozygous pDAS5381 $T_1$ tobacco plants transformed with pDAS5381. The protocols described, supra (Fold Expression Assay), were used for the screening of $T_1$ plants to confirm that the zinc finger nuclease was expressing, and to identify the events which would produce robust quantities of zinc finger nuclease for excising the GUS PTU expression cassette.

Selection of $T_1$ Plants.

$T_1$ pDAS5380 events were screened for zygosity and expression of GUS and GFP. $T_1$ pDAS5381 events were screened for zygosity and expression of Fok1. Based on these results, $T_1$ events were selected for crossing. These events were identified as optimal, as they were homozygous, single copy, full length, transgene-expressing events. In addition, sibling-null pDAS5381 plants were retained for use as controls. These events do not contain the zinc finger nuclease PTU expression cassette. The transgene was not inherited by these $T_1$ plants as a result of transgene segregation. The selected events were grown to maturity and crossed to produce $F_1$ plants to test transgene excision via the zinc finger nuclease. The crossing strategy is set forth below.

Crossing of the Homozygous $T_1$ Plants for Producing an $F_1$.

Selected pDAS5380 plants were crossed with select pDAS5381 plants. In addition, reciprocal crosses were made so that parents were both male and female (Table 2). The plants were crossed by hand; pollen from the anthers of a mature male parent was introduced to the stigma of the mature female parent. Plants ready for crossing were removed from the other plants to reduce the likelihood that unintended pollen would fertilize the female tobacco plants. Female plants were emasculated (anthers removed prior to dehiscence) using forceps ~15-30 minutes prior to being pollinated by the male flower. Flowers were selected for emasculation by observing the anthers and the flower color. Newly opened flowers were bright pink around the edges and the anthers were still closed. Flowers containing anthers which were opened or partially opened were not used. Multiple flowers from a stem of the tobacco plant were emasculated and fertilized. The additional flowers on the stem (e.g., already fertilized pods, old flowers, very young buds, etc.) were removed with forceps to ensure that the only pods to form on the branch were from controlled crosses. The branch was labeled with a pollination tag listing the cross made, how many crosses were made, and the pollination date. The anthers from the male parent were totally removed from the male plant using forceps, and used to fertilize the emasculated female. The dehiscing male anthers were rubbed onto the sticky receptive female stigma until the stigma was coated with pollen. The stigma was coated several times to reduce the chance of any unintended pollen having access to pollinate the female stigma. The seed from the fertilized plants was collected and sewn into soil. The resulting $F_2$ progeny plants were grown in the greenhouse under the conditions described above.

TABLE 2

Crossing experiment matrix.

| | Excisor Events | | |
|---|---|---|---|
| Target Events | 5381-18 | 5381-49 | 5381-56 |
| 5380-03 | 5381-18-17 X 5380-3-6 | 5381-49-16 X 5380-3-12 | 5381-56-5 X 5380-3-21 |
| 5380-18 | 5381-18-22 X 5380-18-17 | 5381-49-16 X 5380-18-22 | 5381-56-37 X 5380-18-22 |
| 5380-46 | 5381-18-17 X 5380-46-15 | 5381-49-10 X 5380-46-15 | 5381-56-5 X 5380-46-15 |
| Null Events | 5381-56-12 X 5380-3-10 and 5380-25-10 | 5381-56-12 X 5380-3-10 and 5380-25-10 | 5381-56-12 X 5380-3-10 and 5380-25-10 |

Example IV: Analysis of $F_1$ Plants for ZFN-Mediated Transgene Deletion

GUS Assay.

The $F_1$ plants were tested for GUS expression by histochemically staining leaf material. The GUS screen was a preliminary test to identify events which had undergone ZFN-mediated transgene deletion. The results of the GUS screen were not intended to be conclusive, but rather an indicator to identify plants for further molecular analysis. The $F_1$ plants were assayed using the protocol described, supra (GUS Expression Assay). The results are listed in Table 3.

TABLE 3

GUS expression in F1 hybrids.

| | | Target Events | | | | | | | |
|---|---|---|---|---|---|---|---|---|---|
| | | 5380-03 | | | 5380-18 | | | 5380-46 | | |
| Excisor Events | Reciprocal Cross | Plants Assayed | GUS− | % | Plants Assayed | GUS− | % | Plants Assayed | GUS− | % |
| 5381-18 | ♀ | 479 | 15 | 3.1 | 490 | 3 | 0.6 | 450 | 7 | 1.6 |
| | ♂ | 459 | 44 | 9.6 | 480 | 21 | 4.4 | — | — | — |
| 5381-49 | ♀ | — | — | — | 452 | 157 | 34.7 | 474 | 32 | 6.8 |
| | ♂ | 465 | 67 | 14.4 | 467 | 17 | 3.6 | 485 | 69 | 14.2 |
| 5381-56 | ♀ | 437 | 4 | 0.9 | 476 | 0 | 0 | 465 | 3 | 0.7 |
| | ♂ | — | — | — | 470 | 7 | 1.5 | 450 | 3 | 0.7 |
| NULL | ♀ | — | — | — | 441 | 8 | 1.8 | 453 | 11 | 2.4 |
| | ♂ | — | — | — | 446 | 4 | 0.9 | 490 | 11 | 2.2 |

Southern Blot Analysis.

Southern blot analysis was used to provide molecular characterization of the excision of the GUS PTU expression cassette by the zinc finger nuclease. This data demonstrated the excision of the GUS PTU expression cassette in a sub-set of events, the non-excision of the GUS PTU expression cassette in another sub-set of events, and a sub-set of chimeric events which contained both excised and non-excised GUS PTU expression cassette. Detailed Southern blot analysis was conducted using a probe specific to the GFP PTU expression cassette. The hybridization of the probe with genomic DNA that had been digested with specific restriction enzymes identified DNA fragments of specific molecular weights. These patterns could be analyzed to identify events that contained an excised GUS PTU expression cassette, contained an intact GUS PTU expression cassette, or were chimeric and contained both the excised and intact GUS PTU expression cassette.

Figure 5:
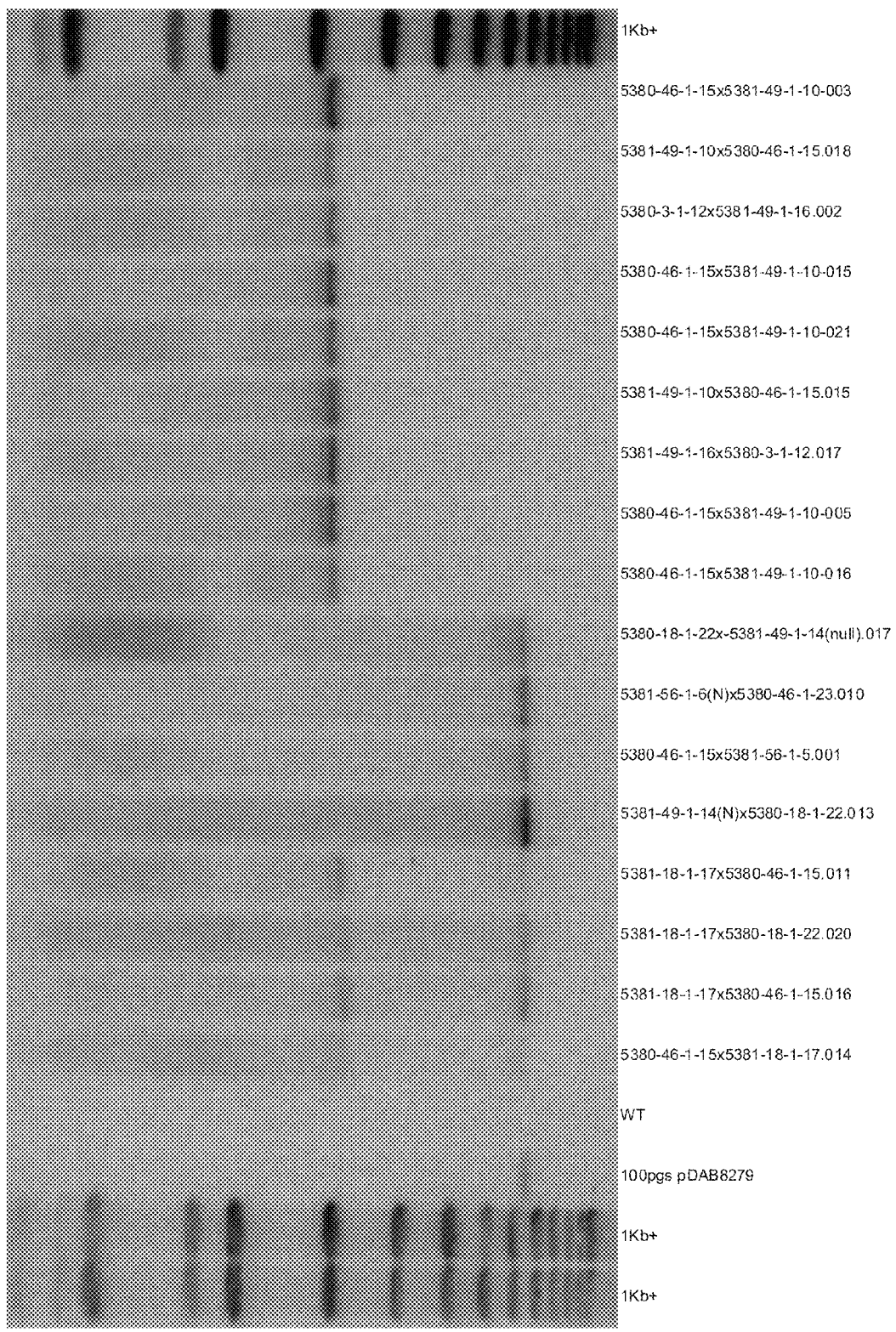
FIG. 5 includes Southern blot analysis of a select group of events that are representative of a larger sample according to an embodiment of the invention. These samples were selected to illustrate the excised fragment (i.e., the lower molecular fragment), the non-excised fragment (i.e., the higher molecular weight fragment), and the chimeric events which contained both the excised and non-excised fragments. In addition, controls of the wild-type genomic DNA and 100 pg of the pDAS5380 plasmid were included. This data correlated with the GUS expression data. Events that did not stain positive via histochemical staining for GUS did not contain a full-length, intact GUS PTU expression cassette.

A restriction digest was completed for 10 µg of each sample in 1× Buffer 4 and 100 Units of NdeI (New England BioLabs, Ipswich, Mass.) in a final volume of 350 µL for a 10-fold over-digestion. Samples were incubated at 37° C. overnight. The digested DNA was concentrated by re-precipitation with Quick Precipitation Solution™ (Edge Biosystems, Gaithersburg, Md.) according to the manufacturer's suggested protocol. Recovered digest was resuspended in 30 µL of 1× loading buffer and incubated at 65° C. for 30 minutes. Resuspended samples were loaded onto a 0.8% agarose gel prepared in 1×TAE (0.8M Tris-acetate [pH 8.0]/0.04 mM EDTA) and electrophoresed overnight at 1.1 V/cm in 1×TAE buffer. The gel was sequentially subjected to denaturation (0.2 M NaOH/0.6 M NaCl) for 30 minutes, and neutralization (0.5 M Tris-HC1 [pH 7.5]/1.5 M NaCl) for 30 minutes. Transfer of DNA fragments was performed by passively wicking 20×SSC solution overnight through the gel onto treated Immobilon™ NY+ (Millipore, Billerica, Mass.) by using a chromatography paper wick and paper towels. Following transfer, the membrane was briefly washed with 2×SSC, cross-linked with the Stratalinker™ 1800 (Stratagene, La Jolla, Calif.), and vacuum baked at 80° C. for 3 hours. Blots were incubated with prehybridization solution for 1 hour at 65° C. in glass roller bottles using a hybridization incubator. Probe was prepared from PCR fragment containing the gfp coding sequence that was purified using a Qiagen gel extraction kit and labeled with 50 µCi of $\alpha^{32}$P-dCTP using a labeling kit. Blots were hybridized overnight at 65° C. with denatured probe added directly to hybridization buffer to approximately 2 million counts per blot per mL. Following hybridization, blots were sequentially washed at 65° C. with 0.1×SSC/0.1% SDS for 40 minutes. Blots were exposed using phosphor imager screen and imaged using a Molecular Dynamics Storm 860™ imaging system. The results of the blots are shown in FIG. 5.

Plant Transcription Unit PCR Analysis.

PCR reactions were performed to characterize the excision of the GUS PTU expression cassette. Primers were designed which bound to the MAR sequence and the ORF 23 3' UTR sequence (the 3' UTR for the GFP PTU expression cassette). This PCR amplicon spans the GUS PTU expression cassette region which is expected to be excised. As such, the use of these PCR primers can detect events in which the GUS PTU expression cassette was excised, events in which no excision occurred, and chimeric events in which the GUS PTU expression cassette was not uniformly removed within the event. Amplification of a 6.7 kb fragment indicates that there is no excision, whereas amplification of a 2.4 kb fragment suggests that the GUS PTU expression cassette had been excised. Amplicons containing fragments of both sizes indicate that the GUS PTU expression cassette was not completely removed.

Figure 6:
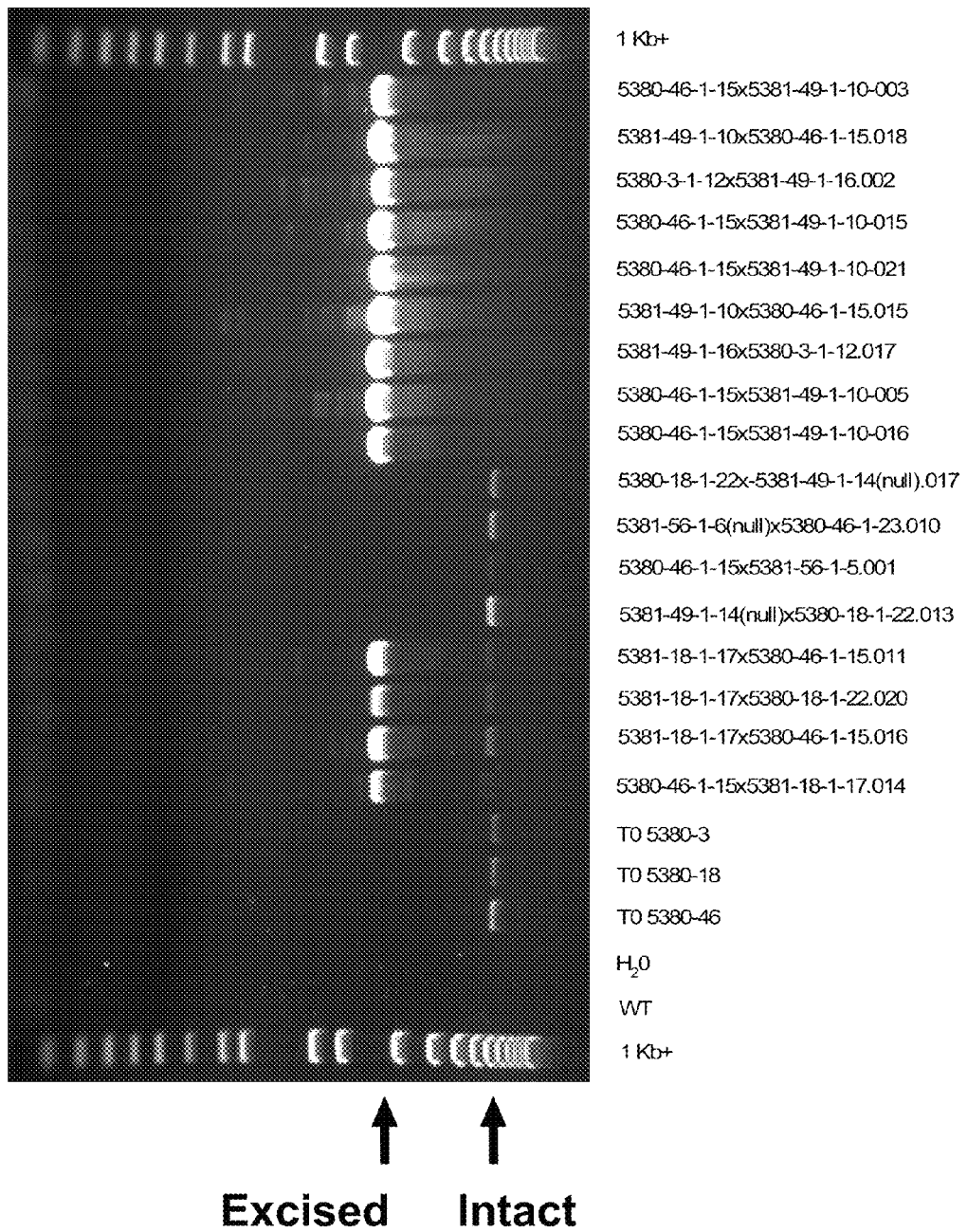
FIG. 6 includes the image of an agarose gel containing PCR amplified fragments of the genomic DNA samples used in the Southern blot experiments according to an embodiment of the invention. These PCR amplicons illustrate the excised fragment (i.e., the lower molecular weight fragment), the non-excised fragment (i.e., the higher molecular weight fragment), and the chimeric events which contained both the excised and non-excised fragments. In addition, controls of the wild $T_0$ plants are included; the larger intact GUS PTU expression cassette was amplified in these reactions. Negative controls where wild-type genomic DNA and no DNA ($H_2O$) were used for the PCR reactions are also included. This data correlated with the GUS expression data and the Southern blot data.

Genomic DNA was isolated from tobacco leaf tissue using the DNeasy™ Plant Maxi kit, and quantified using the Quant-IT™ Pico Green DNA assay kit as described, supra. Plant Transcription Unit PCR (PTU PCR) was performed using a Tetrad2™ thermocycler (BioRad, Hercules, Calif.). Oligonucleotide primers were designed to amplify the PTU using Vector NTI™ Software. For amplification, Ex Taq Polymerase™ (TaKara, Otsu, Shiga, Japan) was prepared at 1× final concentration in a 25 µL, volume singleplex reaction containing 1.2 µM of each primer (SEQ ID NOs:16 and 17), 0.2 mM dNTP, 2% DMSO, 1.25 units of TAQ using 4 ng of gDNA template. A three-step amplification reaction was performed as follows; 3 minute initial denaturation at 94° C. and 33 cycles of 30 seconds of 94° C., 6 minutes of 65.5° C., 30 seconds of 72° C., with a final extension at 72° C. for 10 minutes. An aliquot of the PCR product was run on a 1% gel with ethidium bromide using a 1 Kb+marker (Invitrogen, Carlsbad, Calif.) to determine product size. Results of the PTU PCR reactions are shown in FIG. 6.

Sequencing of PTU PCR Products.

Figure 7A:
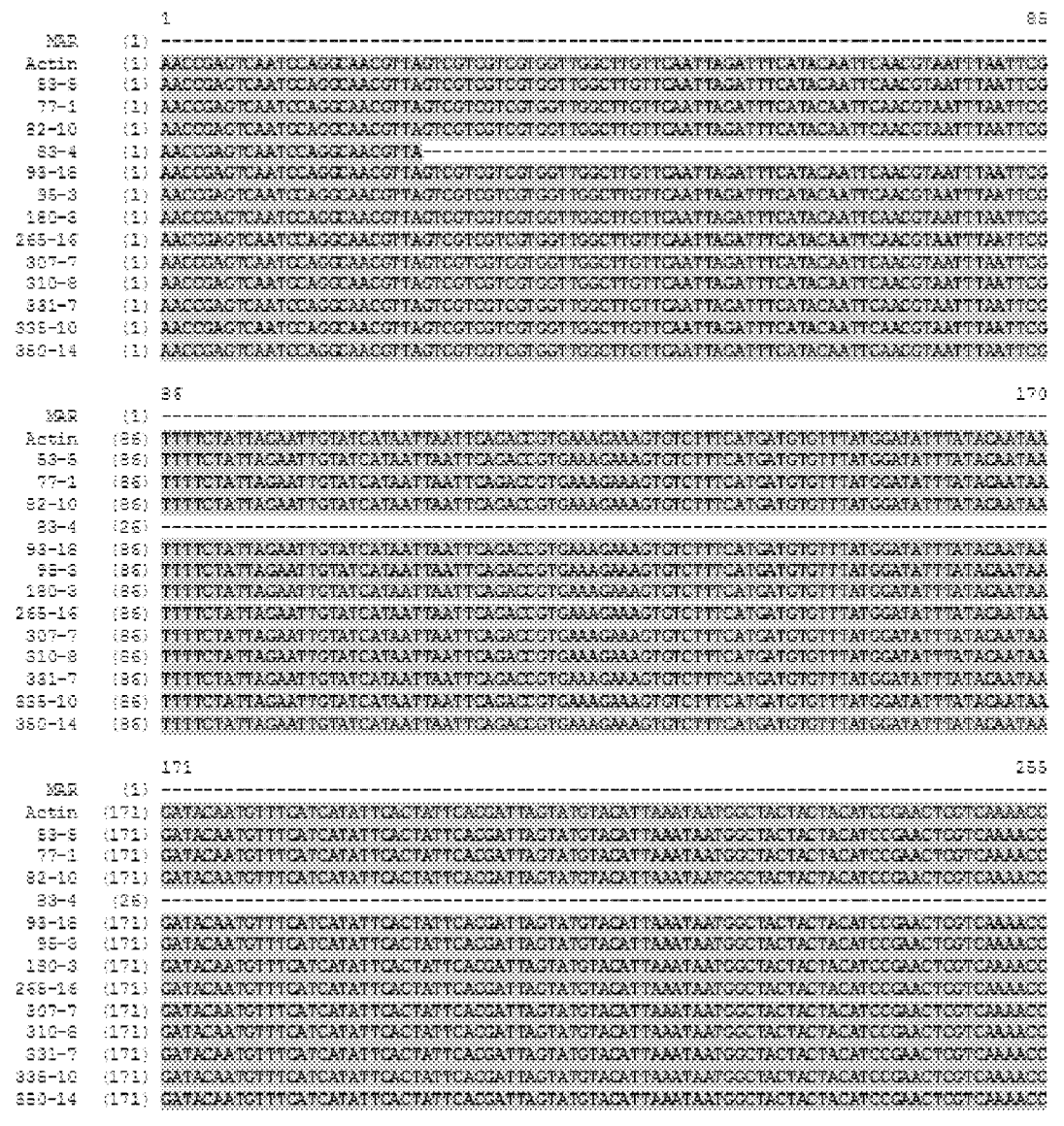
Figure 7A:
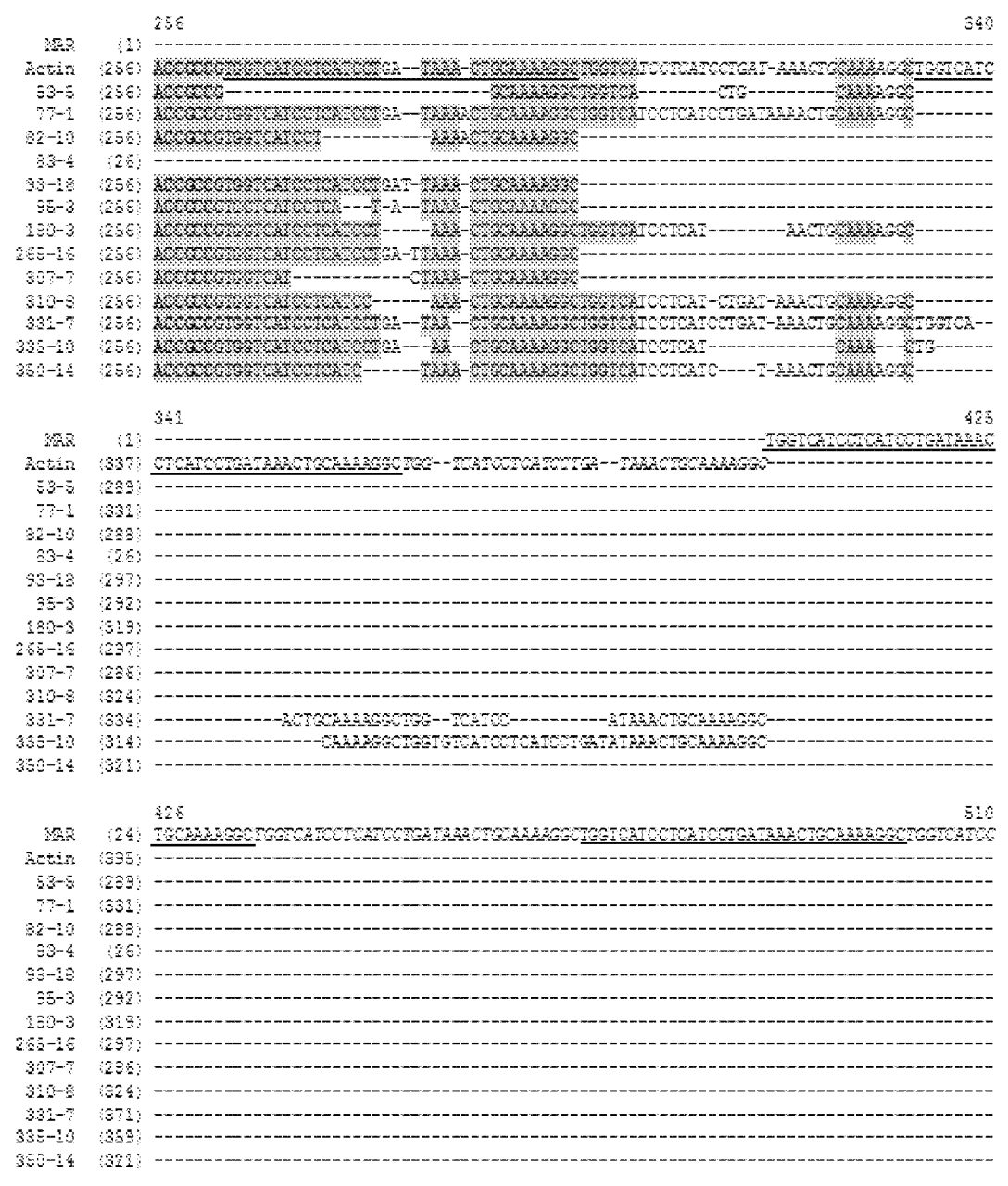
Figure 7B:
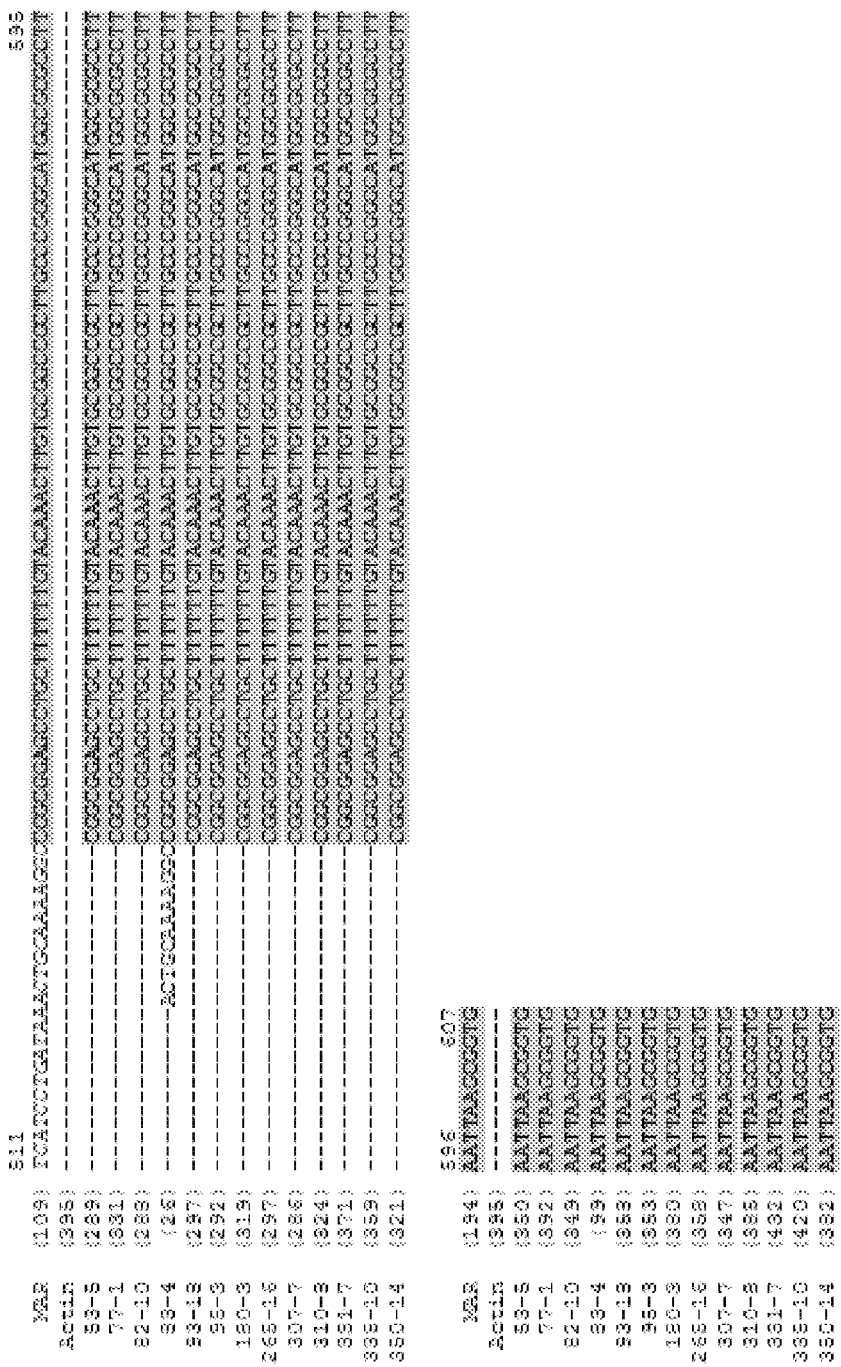
Figure 8:
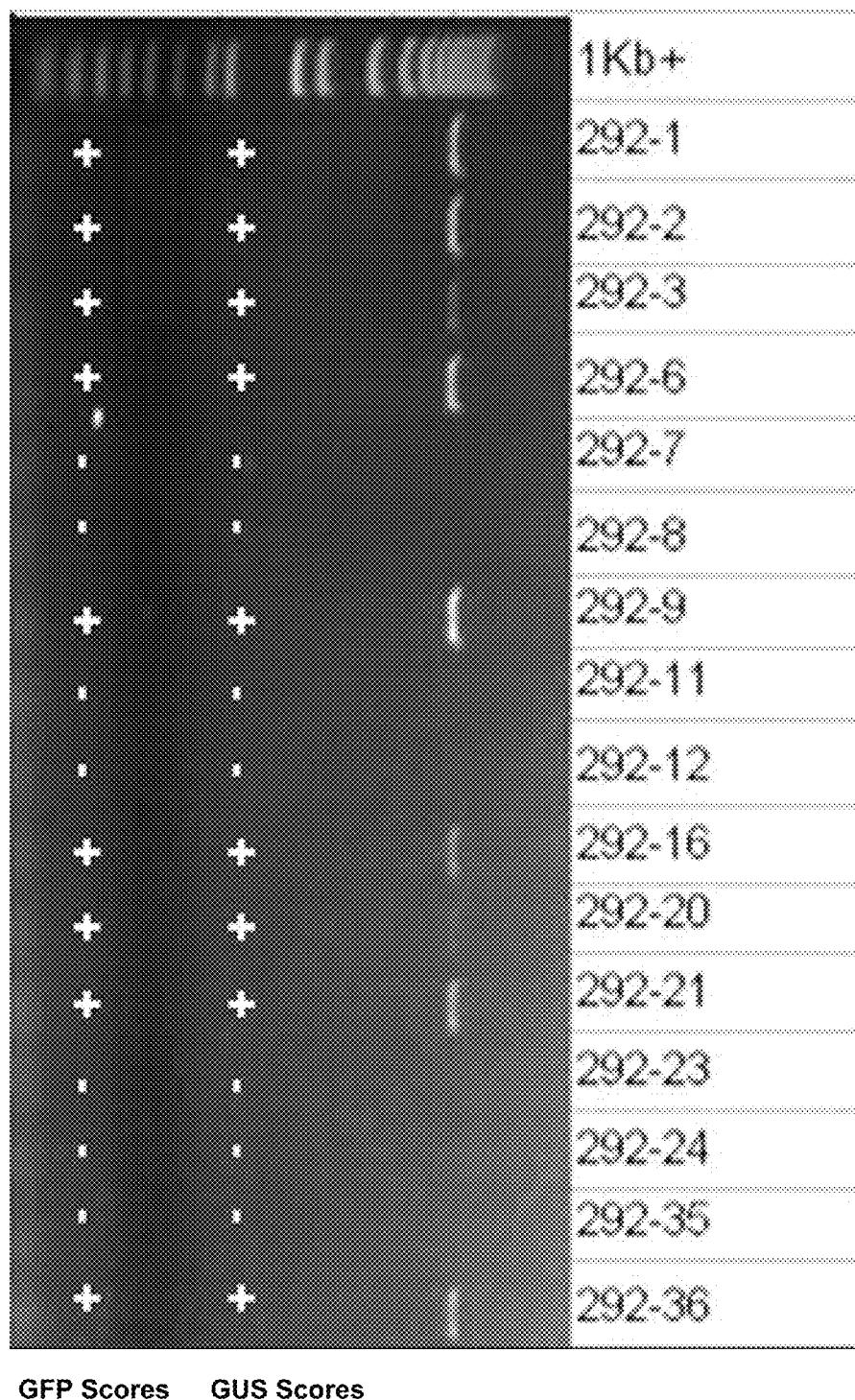
FIG. 8 includes PCR analysis of $F_2$ progenies of "Intact" $F_1$ hybrids according to an embodiment of the invention.
Figure 9:
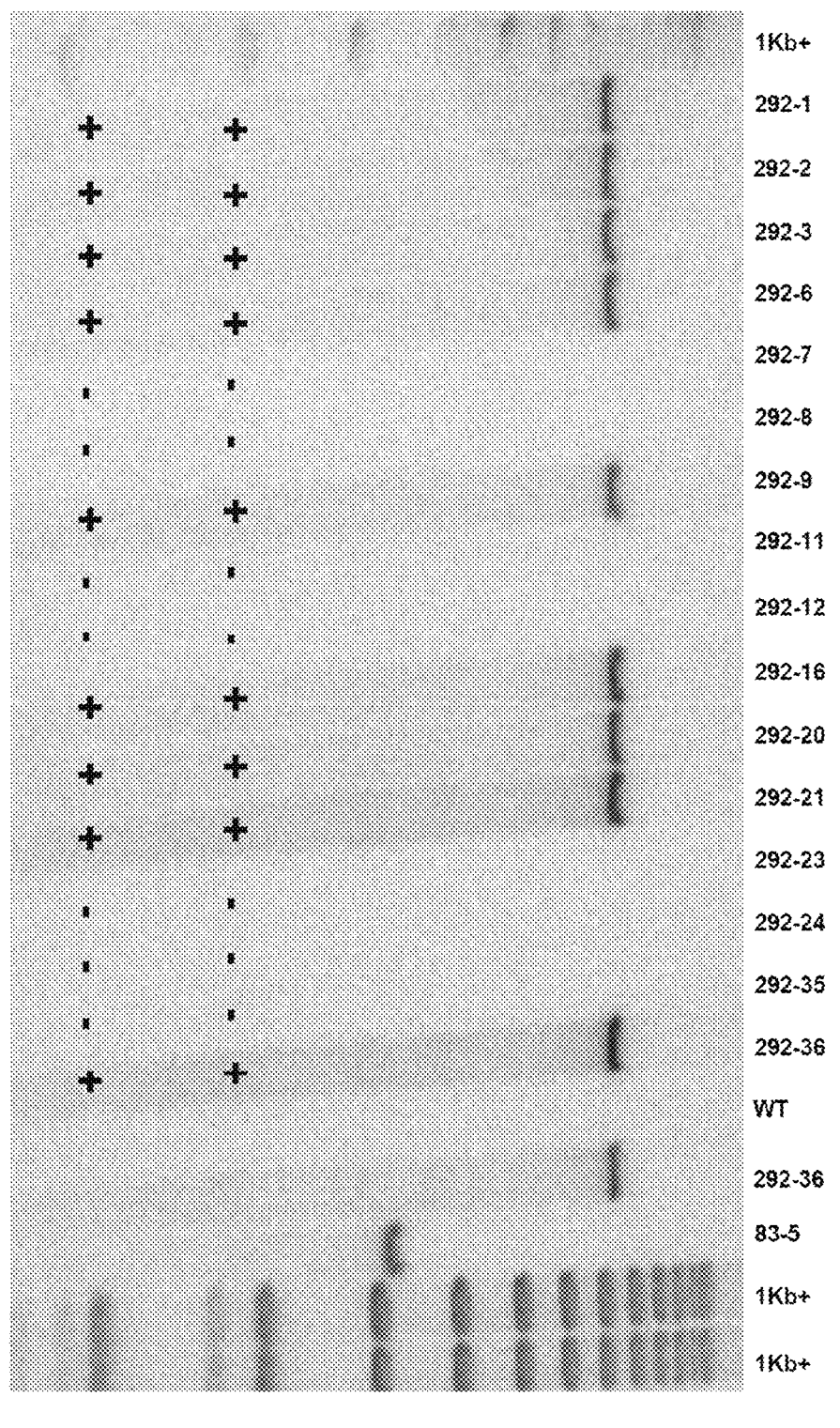
FIG. 9 includes Southern analysis of $F_2$ progenies of "Intact" $F_1$ hybrids according to an embodiment of the invention.
Figure 10:
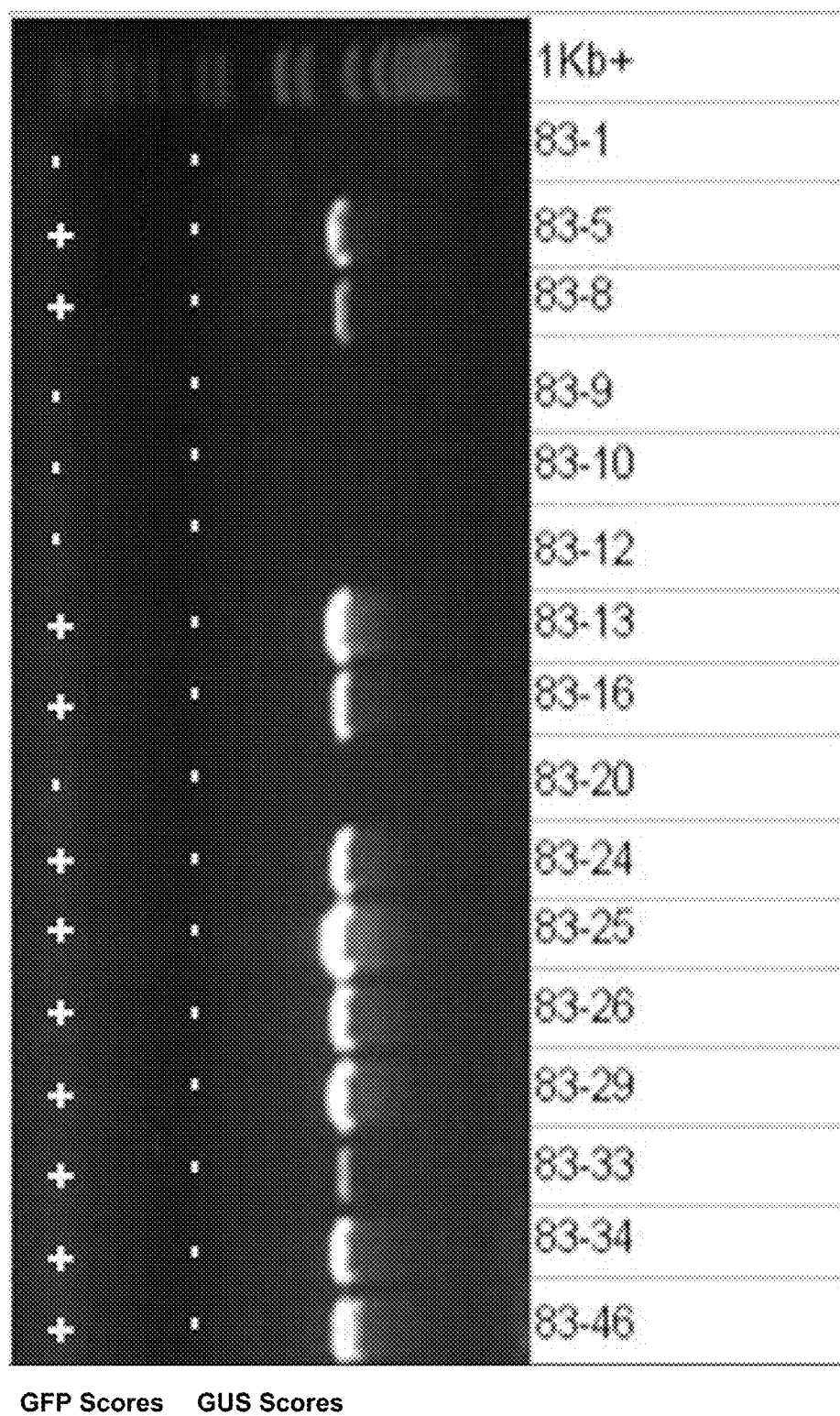
FIG. 10 includes PCR analysis of $F_2$ progenies of "Excised" $F_1$ hybrids according to an embodiment of the invention.
Figure 11:
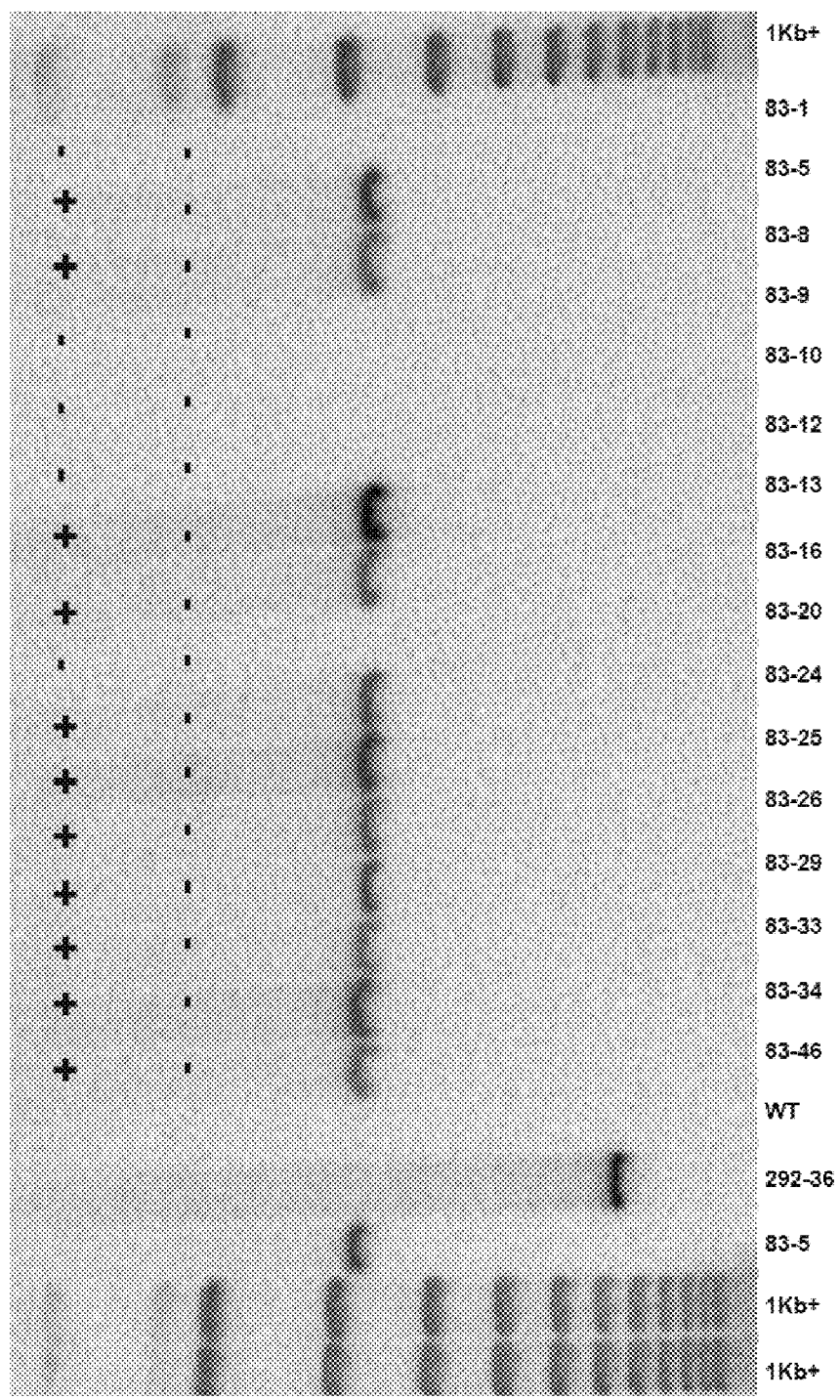
FIG. 11 includes Southern analysis of $F_2$ progenies of "Excised" $F_1$ hybrids according to an embodiment of the invention.
Figure 12:
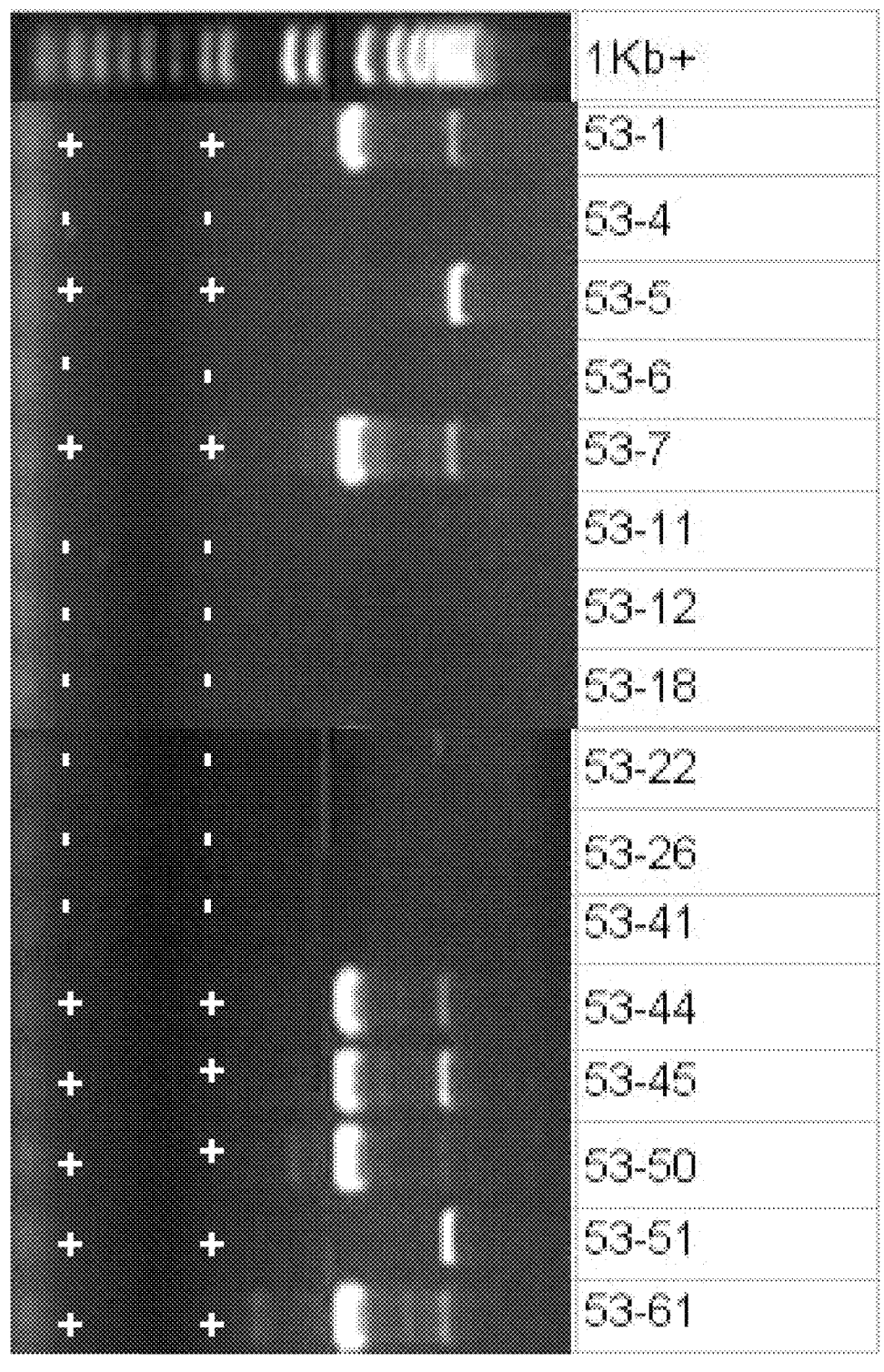
FIG. 12 includes PCR analysis of $F_2$ progenies of "Chimeric" $F_1$ hybrids according to an embodiment of the invention.
Figure 13:
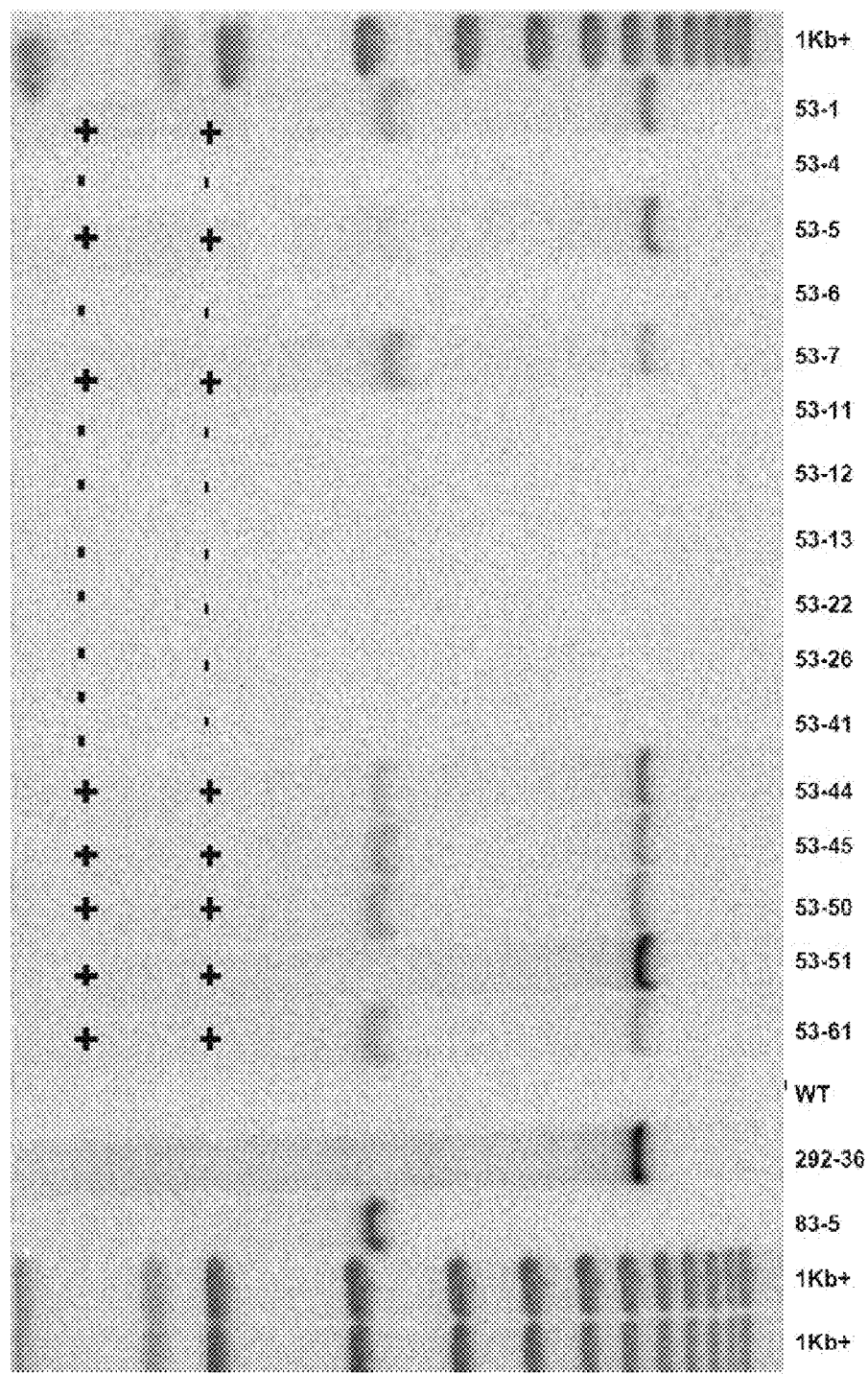
FIG. 13 includes Southern analysis of $F_2$ progenies of "Chimeric" $F_1$ hybrids according to an embodiment of the invention.

The 2.4 kb bands from the PTU PCR reactions were excised from the gel and DNA was purified using the Qiagen Qiaex II™ gel extraction kit (Qiagen, Germantown, Md.). The purified fragments were ligated into the pCR2.1 TOPO-TAT™ cloning vector (Invitrogen, Carlsbad, Calif.). Presence of a cloned PCR amplicon within the pCR2.1 vector was confirmed via restriction enzyme digestion. Clones containing the amplified bands were sequenced. The sequences of the junction resulting from the removal of the GUS PTU expression cassette are listed in FIGS. 7a and 7b. The entire PTU expression cassette was removed. The only sequences remaining are rearranged zinc finger binding sites which flanked the GUS PTU expression cassette. In addition, several PCR amplicons contained deletions which extended into the Actin 2 promoter of the GFP PTU expression cassette.

Restriction Enzyme Analysis of 6.7 kb Band.

The PCR amplicons of the larger 6.7 kb band were analyzed via restriction enzyme digestion. These fragments were digested with EcoRI, and with NcoI/SacI restriction enzymes (New England Biolabs, Ipswich, Mass.). The sizes of the resulting bands were analyzed to confirm that the amplified fragments spanned the non-excised pDAS5380 transgene genomic insert.

Self-Fertilization of $F_1$ Plants to Produce $F_2$ Progenies.

A representative group of the $F_1$ plants described above were self-fertilized to produce $F_2$ progenies. Table 5 lists the plants that were selected and their $F_1$ phenotype and genotype. Selected $F_1$ plants were grown in a greenhouse under a 16:8-hour photoperiod, with daytime and nighttime temperature between 22-24° C. When the primary flowering stem began to elongate and form flower buds, the entire plant was covered with a selfing bag to prevent out-crossing. Seeds derived from self-pollination were harvested about eight weeks after transplanting. The seed from the self-fertilized plants was collected and sewn into soil. The resulting $F_2$ populations were grown in the greenhouse under the conditions described above. The $F_2$ plants were analyzed for further transgene deletion and heritability of the deletion which had been characterized within $F_1$ plants.

Example V: Generation and Selection of $T_1$ Plants

Analysis of $F_2$ Progenies for Transgene and Heritability of Deletion.

GUS Analysis.

The $F_2$ plants were tested for GUS expression by histochemical staining of leaf material. The plants were assayed using the protocol described, supra (GUS Expression Assay). The results are listed in Table 5. The GUS expression data from the $F_2$ plants were as expected. The $F_1$ plants that were identified as containing an excised GUS PTU expression cassette produced $F_2$ plants that were 100% GUS negative, as confirmed by histochemical staining. The absence of the GUS expression within these $F_2$ plants confirms the $F_1$ data, which suggests that the GUS PTU expression cassette was excised via zinc finger nuclease-mediated transgene deletion. Moreover, this data exemplifies the heritability of the deleted transgene into a subsequent generation.

The sibling-null control plants expressed GUS in about 75% of the $F_2$ generation. The remaining plants (about 25%) in which GUS was not detected via histochemical staining were expected. The GUS PTU expression cassette is expected to segregate within the $F_2$ population at the expected 3:1 ratio. The chimeric events which contained both excised and non-excised GUS PTU expression cassettes in the $F_1$ segregated within the $F_2$. The majority of the plants expressed GUS.

TABLE 5

GUS expression in the F2 progenies.

| Cross # | Cross Identity | F1 Molecular/Phenotypic Characterization | # Plants Assayed | # GUS+ | # GUS− |
|---|---|---|---|---|---|
| 95 | 5380-46-1-15x5381-49-1-10-003 | Excised/GUS− | 405 | 0 | 405 |
| 307 | 5381-49-1-10x5380-46-1-15.018 | Excised/GUS− | 480 | 0 | 480 |
| 180 | 5380-3-1-6x5381-18-1-17.002 | Excised/GUS− | 445 | 0 | 445 |
| 83 | 5380-46-1-15x5381-49-1-10-015 | Excised/GUS− | 375 | 0 | 375 |
| 77 | 5380-46-1-15x5381-49-1-10-021 | Excised/GUS− | 427 | 0 | 427 |
| 310 | 5381-49-1-10x5380-46-1-15.015 | Excised/GUS− | 442 | 0 | 442 |
| 265 | 5381-49-1-16x5380-3-1-12.017 | Excised/GUS− | 471 | 0 | 471 |
| 93 | 5380-46-1-15x5381-49-1-10-005 | Excised/GUS− | 386 | 0 | 386 |
| 4 | 5380-18-1-22x5381-49-1-14(null).017 | Intact/GUS+ (null) | 473 | 356 | 117 |
| 214 | 5381-56-1-6(null)x5380-46-1-23.010 | Intact/GUS+ (null) | 480 | 377 | 102 |
| 292 | 5381-49-1-14(null)x5380-18-1-22.013 | Intact/GUS+ (null) | 481 | 370 | 111 |
| 189 | 5380-46-1-15x5381-56-1-5.001 | Intact/GUS+ | 456 | 345 | 111 |
| 335 | 5381-18-1-17x5380-46-1-15.011 | Chimeric/GUS+ | 449 | 326 | 123 |
| 350 | 5381-18-1-17x5380-18-1-22.020 | Chimeric/GUS+ | 457 | 342 | 114 |
| 331 | 5381-18-1-17x5380-46-1-15.016 | Chimeric/GUS+ | 452 | 347 | 104 |
| 53 | 5380-46-1-15x5381-18-1-17.014 | Chimeric/GUS+ | 470 | 359 | 109 |

Green Fluorescent Protein ELISA Analysis.

Selected $F_2$ plants were tested for GFP expression by ELISA using the protocol described, supra (GFP Expression Assay). GFP expression data from the $F_2$ plants were as expected. The $F_1$ plants expressed GFP in about 75% of the $F_2$ generation. The remaining plants (about 25%) in which GFP was not detected via ELISA was expected. The GFP PTU expression cassette is expected to segregate within the $F_2$ population at the expected 3:1 ratio. The chimeric events which contained both excised and non-excised GFP PTU expression cassettes in the $F_1$ segregated within the $F_2$. The majority of the plants expressed GFP.

PCR, Southern Blot, and GFP Analysis of $F_2$ Progenies.

Sixteen plants from three of the crosses listed in Table 5 (representing excised, intact, and chimeric progenies) were kept for further molecular analysis. These sixteen plants consisted of eight plants that were GUS positive and eight plants that were GUS negative for the sibling null control and chimeric plants. The protocols described, supra (Southern Blot Analysis; and Plant Transcription Unit PCR Analysis), were repeated with genomic DNA from the $F_2$ plants. Selected $F_2$ plants were tested for GFP expression by ELISA using the protocol described, supra (GFP Expression Assay). The molecular data confirm that plants which did not express GUS do not contain the intact GUS PTU expression cassette. GFP expression segregated as expected. The results are summarized in FIGS. 8-13.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All references, including publications, patents, and patent applications, cited herein are hereby incorporated by reference to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

What is claimed is:

1. An isolated nucleic acid molecule comprising:
a promoter; and
a nucleic acid sequence encoding a zinc finger nuclease, wherein the promoter is operably linked to the nucleic acid sequence encoding the zinc finger nuclease, wherein the nucleic acid sequence is flanked by zinc finger nuclease cleavage sites.

2. A method of producing a transgenic plant comprising:
transforming a plant cell or plant tissue with the isolated nucleic acid molecule of claim 1; and
regenerating a whole plant.

3. The isolated nucleic acid molecule of claim 1, wherein the promoter is selected from the group consisting of: a pollen-specific promoter, a seed-specific promoter, and a developmental-stage specific promoter.

4. A method for deleting a polynucleotide in a plant, the method comprising:
crossing a first viable plant and a second viable plant such that F1 seed is produced on either the first or the second viable plant;
wherein the first viable plant is a plant produced by the method according to claim 2; and
wherein the second viable plant comprises genomic DNA comprising, in the 5' to 3' direct: a first cleavage site for the zinc finger nuclease, the polynucleotide, and a second cleavage site for the zinc finger nuclease; and
growing a resultant transgenic F1 plant, wherein the polynucleotide is absent from the genomic DNA.

5. The method of claim 4, wherein the first cleavage site for the zinc finger nuclease and the second cleavage site for the zinc finger nuclease are identical.

6. The transgenic plant produced by the method of claim 4.

7. A method for deleting a region of DNA in a plant cell, the method comprising:
providing a nucleic acid comprising a first polynucleotide which is recognized and cleaved by a zinc finger nuclease, a selectable marker gene expression cassette, and a second polynucleotide which is recognized and cleaved by a zinc finger nuclease, wherein the selectable marker is flanked by the first and second polynucleotides,
wherein the nucleic acid of claim 1 is introduced into the plant cell and either the first or the second polynucleotide is recognized and cleaved by the zinc finger nuclease encoded by the nucleic acid of claim 1, so as to cleave the DNA at either the first or the second polynucleotide,
thereby resulting in the excision of the selectable marker from the DNA.

8. The method of claim 7, wherein the first polynucleotide and the second polynucleotide are flanked by polynucleotides capable of homologous recombination with each other.

9. The method of claim 7, further comprising introducing into the plant cell a zing finger nuclease that recognizes and cleaves either the first or the second polynucleotide.

10. The method according to claim 7, wherein the first and second polynucleotides are the same.

11. The method according to claim 4, wherein the first and second cleavage sites for the zinc finger nuclease are flanked by polynucleotides capable of homologous recombination with each other.

12. A method of excising a native gene of interest in a plant comprising:
transforming a plant cell or tissue comprising a gene of interest with an isolated nucleic acid molecule encoding a zinc finger nuclease, wherein the zinc finger nuclease recognizes and cleaves at a first polynucleotide positioned 5' with respect to the native gene of interest; and
wherein the zinc finger nuclease recognizes and cleaves at a second polynucleotide positioned 3' with respect to the native gene of interest; and
regenerating a whole plant.

13. The method according to claim 12, wherein the first and second polynucleotides recognized and cleaved by the zinc finger nuclease are flanked by polynucleotides capable of homologous recombination with each other.

* * * * *

SEQUENCE LISTING

```
<160> NUMBER OF SEQ ID NOS: 18

<210> SEQ ID NO 1
<211> LENGTH: 33
<212> TYPE: DNA
<213> ORGANISM: Artificial Sequence
<220> FEATURE:
<223> OTHER INFORMATION: CCR5 ZFN binding site

<400> SEQUENCE: 1
tggtcatcct catcctgata aactgcaaaa ggc                                   33

<210> SEQ ID NO 2
<211> LENGTH: 2139
<212> TYPE: DNA
<213> ORGANISM: Artificial Sequence
<220> FEATURE:
```

<223> OTHER INFORMATION: CCR5 Zinc Finger Nuclease gene sequence

<400> SEQUENCE: 2

```
atggctccaa ggaagaggaa ggagtctaac agggagtcag ctaggaggtc aaggtacagg      60
aaggtgggta tccacggggt acccgccgct atggccgaga ggcccttcca gtgtcgaatc     120
tgcatgcgta acttcagtga ccgctccaac ctgtcccgcc acatccgcac ccacacaggc     180
gagaagcctt ttgcctgtga catttgtggg aggaagtttg ccatctcctc caacctgaac     240
tcccatacca agatacacac gggatctcag aagcccttcc agtgtcgaat ctgcatgcgt     300
aacttcagtc gctccgacaa cctggcccgc acatccgca cccacacagg cgagaagcct      360
tttgcctgtg acatttgtgg gaggaagttt gccacctccg gcaacctgac ccgccacgcc     420
cagcgctgcg gcggcctgcg gggatcccaa cttgtgaaat cagaattgga agagaaaaag     480
tctgagctta gacacaaatt gaagtacgtt ccacatgaat atatcgaact tatcgagatt     540
gctaggaact caacacagga cagaattttg gagatgaagg ttatggagtt ctttatgaaa     600
gtgtacggat atagggaaa gcaccttggt ggttctagga aacctgatgg tgcaatctac      660
actgtgggat cacctattga ctatggtgtt atcgtggata caaaggcata ctctggtgga     720
tacaatttgc caatcggaca agctgacgaa atggagagat atgttgaaga gaaccaaact     780
agaaacaaac atcttaatcc aaatgaatgg tggaaggtgt atccttcatc tgttacagag     840
ttcaaattcc ttttttgtgtc tggacactt aagggtaact acaaagcaca gcttactagg      900
ttgaaccata ttacaaattg caatggtgct gtgttgtcag ttgaagagct tttgatcgga     960
ggtgaaatga ttaaggcagg aacacttact ttggaggaag ttagaagaaa attcaacaac    1020
ggtgaaatca attttagatc tggcggcgga gagggcagag aagtcttct aacatgcggt     1080
gacgtggagg agaatcccgg ccctaggatg gctccaagga gaggaagga gtctaacagg    1140
gagtcagcta ggaggtcaag gtacaggaag gtgggtatcc acggggtacc cgccgctatg    1200
gccgagaggc ccttccagtg tcggatctgc atgcggaact tcagcaggag cgacaacctg    1260
agcgtacaca tccgcaccca cacaggcgag aagccttttg cctgtgacat tgtggggagg   1320
aaatttgccc agaaaatcaa cctccaggtc cacaccaaga tccacaccgg agagaagccc   1380
tttcagtgca gaatctgcat gagaaacttc tcccggtccg acgtgctgag cgagcacatt   1440
aggacccaca ccggggagaa acccttcgcc tgcgacatct gtggccgcaa atttgcccag   1500
cgcaaccacc ggacaacaca cgcccagcgc tgcggcggcc tgcggggatc ccaacttgtg   1560
aaatcagaat tggaagagaa aaagtctgag cttagacaca aattgaagta cgttccacat   1620
gaatatatcg aacttatcga gattgctagg aactcaacac aggacagaat tttggagatg   1680
aaggttatgg agttctttat gaaagtgtac ggatataggg aaagcaccct tggtggttct   1740
aggaaacctg atggtgcaat ctacactgtg ggatcaccta ttgactatgg tgttatcgtg   1800
gatacaaagg catactctgg tggatacaat ttgccaatcg acaagctga cgaaatgcag     1860
agatatgtta agagaaacca aactagaaac aaacatatta tccaaatga atggtggaag    1920
gtgtatcctt catctgttac agagttcaaa ttccttttg tgtctggaca ctttaagggt    1980
aactacaaag cacagcttac taggttgaac cataagacaa attgcaatgg tgctgtgttg   2040
tcagttgaag agcttttgat cggaggtgaa atgattaagg caggaacact tactttggag   2100
gaagttagaa gaaaattcaa caacggtgaa atcaattttt                         2139
```

<210> SEQ ID NO 3
<211> LENGTH: 29

```
<212> TYPE: DNA
<213> ORGANISM: Artificial Sequence
<220> FEATURE:
<223> OTHER INFORMATION: TQPATS primer

<400> SEQUENCE: 3
acaagagtgg attgatgatc tagagaggt                                    29

<210> SEQ ID NO 4
<211> LENGTH: 29
<212> TYPE: DNA
<213> ORGANISM: Artificial Sequence
<220> FEATURE:
<223> OTHER INFORMATION: TQPATA primer

<400> SEQUENCE: 4
ctttgatgcc tatgtgacac gtaaacagt                                    29

<210> SEQ ID NO 5
<211> LENGTH: 29
<212> TYPE: DNA
<213> ORGANISM: Artificial Sequence
<220> FEATURE:
<223> OTHER INFORMATION: TQPATFQ primer

<400> SEQUENCE: 5
ggtgttgtgg ctggtattgc ttacgctgg                                    29

<210> SEQ ID NO 6
<211> LENGTH: 30
<212> TYPE: DNA
<213> ORGANISM: Artificial Sequence
<220> FEATURE:
<223> OTHER INFORMATION: TQPALS primer

<400> SEQUENCE: 6
tactatgact tgatgttgtg tggtgactga                                   30

<210> SEQ ID NO 7
<211> LENGTH: 28
<212> TYPE: DNA
<213> ORGANISM: Artificial Sequence
<220> FEATURE:
<223> OTHER INFORMATION: TQPALA primer

<400> SEQUENCE: 7
gagcggtcta aattccgacc cttatttc                                     28

<210> SEQ ID NO 8
<211> LENGTH: 33
<212> TYPE: DNA
<213> ORGANISM: Artificial Sequence
<220> FEATURE:
<223> OTHER INFORMATION: TQPALFQ primer

<400> SEQUENCE: 8
aaacgatggc aggagtgccc ttttctatc aat                                33

<210> SEQ ID NO 9
<211> LENGTH: 19
<212> TYPE: DNA
<213> ORGANISM: Artificial Sequence
<220> FEATURE:
<223> OTHER INFORMATION: HPT2S primer

<400> SEQUENCE: 9
```

```
acactacatg gcgtgattt                                                    19

<210> SEQ ID NO 10
<211> LENGTH: 18
<212> TYPE: DNA
<213> ORGANISM: Artificial Sequence
<220> FEATURE:
<223> OTHER INFORMATION: HPT2A primer

<400> SEQUENCE: 10
agcatcagct catcgaga                                                     18

<210> SEQ ID NO 11
<211> LENGTH: 19
<212> TYPE: DNA
<213> ORGANISM: Artificial Sequence
<220> FEATURE:
<223> OTHER INFORMATION: HPTFQ primer

<400> SEQUENCE: 11
actgtgatgg acgacaccg                                                    19

<210> SEQ ID NO 12
<211> LENGTH: 21
<212> TYPE: DNA
<213> ORGANISM: Artificial Sequence
<220> FEATURE:
<223> OTHER INFORMATION: Fok1_UPL_F primer

<400> SEQUENCE: 12
tgaatggtgg aaggtgtatc c                                                 21

<210> SEQ ID NO 13
<211> LENGTH: 25
<212> TYPE: DNA
<213> ORGANISM: Artificial Sequence
<220> FEATURE:
<223> OTHER INFORMATION: Fok1_UPL_R primer

<400> SEQUENCE: 13
aagctgtgct ttgtagttac cctta                                             25

<210> SEQ ID NO 14
<211> LENGTH: 21
<212> TYPE: DNA
<213> ORGANISM: Artificial Sequence
<220> FEATURE:
<223> OTHER INFORMATION: BY2ACT89S primer

<400> SEQUENCE: 14
cccagatcat gtttgagacc t                                                 21

<210> SEQ ID NO 15
<211> LENGTH: 21
<212> TYPE: DNA
<213> ORGANISM: Artificial Sequence
<220> FEATURE:
<223> OTHER INFORMATION: BY2ACT89A primer

<400> SEQUENCE: 15
ggaagcgcat atccctcata g                                                 21

<210> SEQ ID NO 16
<211> LENGTH: 24
<212> TYPE: DNA
<213> ORGANISM: Artificial Sequence
```

```
<220> FEATURE:
<223> OTHER INFORMATION: Forward PCR primer for PTU PCR analysis

<400> SEQUENCE: 16
tgggctgaat tgaagacatg ctcc                                           24

<210> SEQ ID NO 17
<211> LENGTH: 22
<212> TYPE: DNA
<213> ORGANISM: Artificial Sequence
<220> FEATURE:
<223> OTHER INFORMATION: Reverse PCR primer for PTU PCR analysis

<400> SEQUENCE: 17
tctgaaaata gtggccaccg ct                                             22

<210> SEQ ID NO 18
<211> LENGTH: 28
<212> TYPE: DNA
<213> ORGANISM: Artificial Sequence
<220> FEATURE:
<223> OTHER INFORMATION: BYACTFQ primer

<400> SEQUENCE: 18
ctagtggtcg tactactggt attgtgct                                       28
```